(12) United States Patent
Forbes et al.

(10) Patent No.: US 12,318,476 B2
(45) Date of Patent: Jun. 3, 2025

(54) MACROPHAGE-BASED THERAPY

(71) Applicant: THE UNIVERSITY COURT OF THE UNIVERSITY OF EDINBURGH, Edinburgh (GB)

(72) Inventors: Stuart Forbes, Edinburgh (GB); John Campbell, Edinburgh (GB); Neil W. A. McGowan, Edinburgh (GB); Alasdair R. Fraser, Edinburgh (GB)

(73) Assignee: THE UNIVERSITY COURT OF THE UNIVERSITY OF EDINBURGH (GB)

( * ) Notice: Subject to any disclaimer, the term of this patent is extended or adjusted under 35 U.S.C. 154(b) by 1025 days.

(21) Appl. No.: 16/980,782

(22) PCT Filed: Mar. 15, 2019

(86) PCT No.: PCT/GB2019/050729
§ 371 (c)(1),
(2) Date: Sep. 14, 2020

(87) PCT Pub. No.: WO2019/175595
PCT Pub. Date: Sep. 19, 2019

(65) Prior Publication Data
US 2020/0405757 A1      Dec. 31, 2020

(30) Foreign Application Priority Data

Mar. 16, 2018   (GB) .................................. 1804255

(51) Int. Cl.
*A61K 9/00* (2006.01)
*A61K 40/17* (2025.01)
(Continued)

(52) U.S. Cl.
CPC ............ *A61K 9/0019* (2013.01); *A61K 40/17* (2025.01); *A61K 40/24* (2025.01); *A61K 40/40* (2025.01);
(Continued)

(58) Field of Classification Search
CPC ...... A61K 35/15; A61K 9/0019; A61K 35/28; C12N 5/0645; C12N 2501/22;
(Continued)

(56) References Cited

U.S. PATENT DOCUMENTS

2015/0125950 A1    5/2015   Lim et al.

FOREIGN PATENT DOCUMENTS

| CN | 105412153 A | 3/2016 |
|---|---|---|
| CN | 107075470 A | 8/2017 |

(Continued)

OTHER PUBLICATIONS

EudraCT Clinical Trial No. 2015-000963-15 and FAQ (Year: 2016).*
(Continued)

*Primary Examiner* — Jeremy C Flinders
*Assistant Examiner* — Thomas R. Amick
(74) *Attorney, Agent, or Firm* — Morrision & Foerster LLP

(57) ABSTRACT

The present invention relate to autologous isolated unpolarized human macrophages for use in the treatment of liver disease and macrophages for use in a method of treating fibrosis in a human in need thereof.

17 Claims, 12 Drawing Sheets

Figure 1:
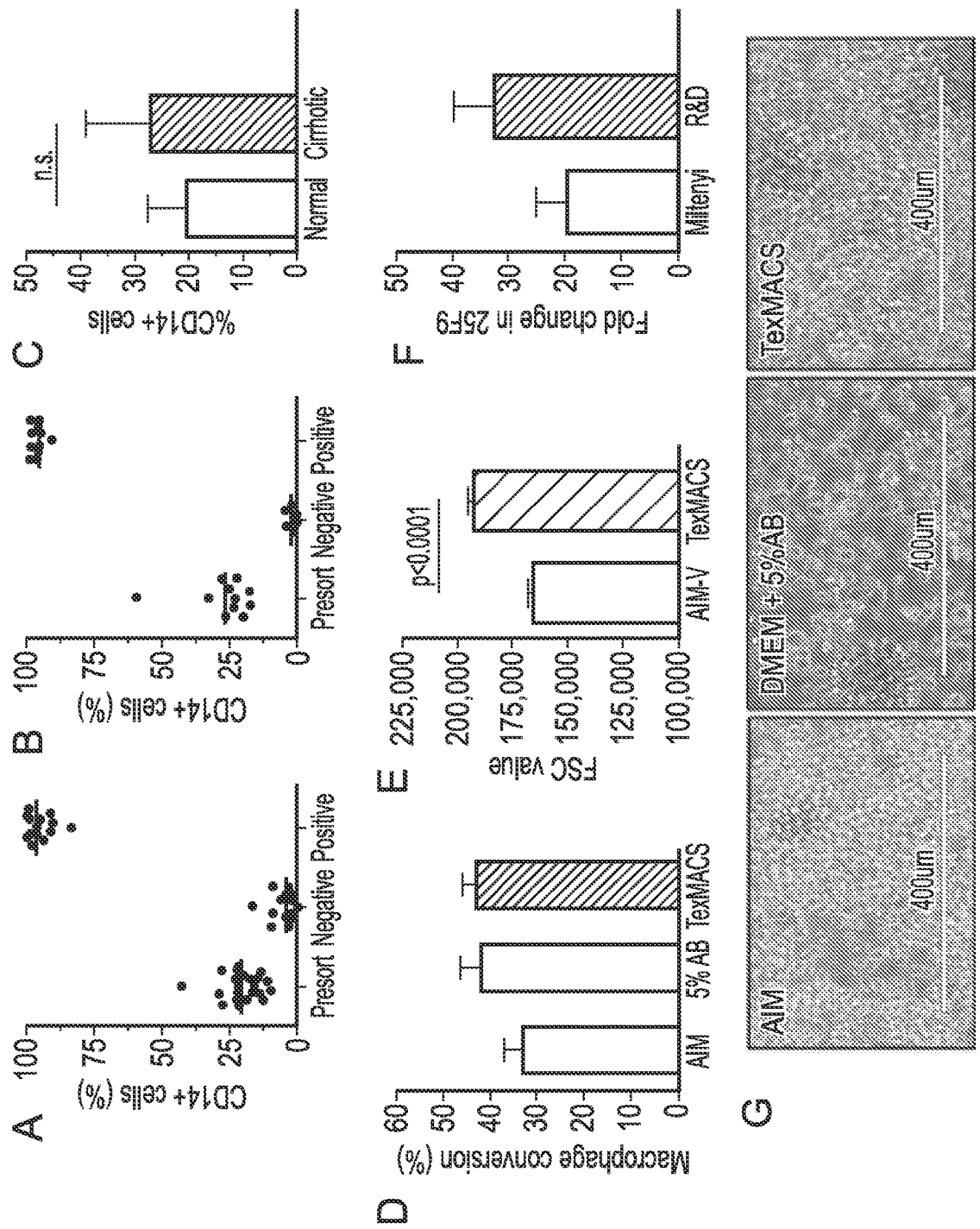

(51) Int. Cl.
A61K 40/24 (2025.01)
A61K 40/40 (2025.01)
C12N 5/0786 (2010.01)

(52) U.S. Cl.
CPC ........ *C12N 5/0645* (2013.01); *A61K 2239/38* (2023.05); *C12N 2501/22* (2013.01); *C12N 2506/02* (2013.01); *C12N 2506/115* (2013.01); *C12N 2506/1353* (2013.01); *C12N 2506/45* (2013.01)

(58) Field of Classification Search
CPC .......... C12N 2506/02; C12N 2506/115; C12N 2506/1353; C12N 2506/45; A61P 1/16
See application file for complete search history.

(56) References Cited

FOREIGN PATENT DOCUMENTS

WO 02059279 A2 8/2002
WO 2018051136 A1 3/2018

OTHER PUBLICATIONS

Murray et al, "Macrophage Activation and polarization: Nomenclature and Experimental Guidelines", Immunity vol. 41, Issue 2, Jul. 17, 2014, p. 339-340. (Year: 2014).*
Thomas et al, Macrophage therapy for murine liver fibrosis recruits host effector cells improving fibrosis, regeneration, and function. Hepatology, 53: 2003-2015. (Year: 2015).*
Kamath (Kamath, Patrick et al., ; D'Amico, Gennaro3; Dickson, Rolland E.1; Kim, Ray W. M.D., M.B.A .*,1,2. A Model to Predict Survival in Patients With End-Stage Liver Disease. Hepatology 33(2):p. 464-470, Feb. 2001) (Year: 2001).*
Terai (Terai, S., Tsuchiya, A. Status of and candidates for cell therapy in liver cirrhosis: overcoming the "point of no return" in advanced liver cirrhosis. J Gastroenterol 52, 129-140 (2017)) (Year: 2017).*
Andersen et al. "Macrophage-related serum biomarkers soluble CD163 (sCD163) and soluble mannose receptor (sMR) to differentiate mild liver fibrosis from cirrhosis in patients with chronic hepatitis C: a pilot study" Eur. J. Clin. Microbiol. Infect. Dis 33:117-122 (Aug. 10, 2013).
Fraser et al. "Development, functional characterization and validation of methodology for GMP-compliant manufacture of phagocytic macrophages: A novel cellular therapeutic for liver cirrhosis" Cytotherapy 19(9):1113-1124 (Sep. 1, 2017).
Martini et al. "Role of SerpinB3 in the stimulation of macrophage activation marker sCD163 in HCV infected patients" 20th National Congress of Digestive Diseases/Digestive and Liver Disease 49(1):e6 (Feb. 16, 2017).
Moore et al. "Phenotypic and functional characterization of macrophages with therapeutic potential generated from human cirrhotic monocytes in a cohort study" Cytotherapy 17(11):1604-1616 (Oct. 31, 2015).
Notification of Transmittal of the International Search Report and the Written Opinion of the International Searching Authority, or the Declaration, in corresponding PCT Application No. PCT/GB2019/050729 (May 8, 2019).
Sandahl et al. "Hepatic macrophage activation and the LPS pathway in patients with alcoholic hepatitis: A prospective cohort study" Am J Gastroenterol 109(11):1749-1756 (Nov. 13, 2014).
Yamamoto et al. "Activated liver macrophages in human liver diseases" Journal of Gastroenterology and Hepatology 10(S1):S72-S76 (Jan. 1, 1995).
Search Report corresponding to GB1804255.6; mailed Nov. 20, 2018 (5 pages).
ISRCTN10368050: Macrophages therapy for liver cirrhosis. Retrieved from http://www.isrctn.com/ISRCTN10368050 on Nov. 16, 2018, Jan. 11, 2017.
Adler, M., et al., "Value of the MELD Score for the Assessment of Pre- and Post-Liver Transplantation Survival", Transplantation Proceedings 37: 2863-2864, 2005.
Boulter, Luke, et al., "Differentiation of progenitors in the liver: a matter of local choice", J Clin Invest. 123(5): 1867-1873, 2013.
Boulter, Luke, et al., "Macrophage-derived Wnt opposes Notch signaling to specify hepatic progenitor cell fate in chronic liver disease", Nature Medicine 18(4): 572-579, 2012.
Brennan, Paul, et al., "LBP-007: Beneficial effects of autologous macrophage therapy on clinical outcomes in patients with compensated cirrhosis: extended follow-up data from a randomized controlled phase 2 trial", Journal of Hepatology 80(S1): S81 (Abstract), 2024.
Campbell, John, "The MATCH Study—Autologous Macrophages for the Treatment of Cirrhosis, Meeting abstract for invited presentation INV08 at British Society for Gene and Cell Therapy Annual Conference and Joint UK Regenerative Medicine Platform Meeting.", Human Gene Therapy 28: A3-A4, 2017.
McGowan, N., et al., "GMP Translation, Validation and Cinical Trial Authorisation of a Macrophage Cell Therapy Product for Liver Cirrhosis", Cytotherapy 19(5): S225 (Article. 309), 2017.
Murray, Peter J., et al., "Macrophage activation and polarization: nomenclature and experimental guidelines", Immunity 41(1): 14-20, 2014.
Newsome, Philip Noel, et al., "Granulocyte colony-stimulating factor and autologous CD133-positive stem-cell therapy in liver cirrhosis (REALISTIC): an open-label, randomised, controlled phase 2 trial", Lancet Gastroenterol Hepatol 3: 25-36, 2018.
Tomioka, Haruaki, et al., "M1 and M2 Macrophage Populations: Those Induced and Activated by Mycobacterial Infections", Kekkaku 91(2): 75-82, 2016 (Machine translation).
Xiao, Haiying, et al., "The Role of Macrophage in the Liver Fibrosis", Chinese Journal of Cell Biology 42(4): 705-711, 2020 (English abstract).

* cited by examiner

MACROPHAGE-BASED THERAPY

BACKGROUND TO THE INVENTION

Liver cirrhosis is a major health problem in the Western world. In the UK, liver disease is the fifth leading cause of mortality, with over one million deaths in 2010 was estimated to be as a result of liver cirrhosis. The disease is associated with a high level of morbidity due to the progressive tissue damage, fibrotic scarring and loss of liver function, and the only curative option for end-stage disease is liver transplantation. However, donor organ availability cannot meet demand, and often patients with end-stage liver disease are not eligible for transplantation. Those who do receive transplantation require lifelong immunosuppression with the increased health risks involved. In 2015, it was reported that 611 patients were on the active liver transplant list in the UK. Patients could be waiting up to two years to receive a liver transplant. At one year post-registration 17% of patients were still waiting on the liver transplant list. Likewise, in the US, there are many patients on the liver transplant waiting list (LTWL) who may never identify a donor organ. Around 1700 patients die on the waiting list or are de-listed due to worsening health each year, while around 6500 have been on the list for more than 6 months. Treatment of end stage liver disease is a huge concern globally.

Alternative therapies are urgently required which prevent or delay the transition of liver disease to terminal decompensated stages.

The pathology of liver cirrhosis can be driven by numerous causative agents, including high alcohol consumption, obesity, metabolic disorders, viral infections or autoimmune disease, resulting in the progressive loss of healthy hepatocyte tissue and liver architecture, replaced by myofibroblast-derived fibrotic scarring. It has been increasingly recognised that if the agents driving liver damage are removed e.g. alcohol, viruses etc. then liver fibrosis can be at least partially reversible enabling liver regeneration to occur.

Animal models of liver regeneration post experimental liver damage have shown that macrophages may play a key role in the control and repair of fibrotic liver disease. Macrophages in the liver are a heterogeneous population of cells, including resident Kuppfer cells and recruited haematopoietic-derived macrophages, with diverse roles in the liver's regenerative response after injury including such as phagocytosis, maintaining immune tolerance, both promotion and resolution of inflammation and fibrosis through activation of hepatic stellate cells/production of cytokines and degradation of the extracellular matrix.

A number of macrophage-directed therapeutic approaches to liver diseases have been reported (as reviewed for example in Tacke et al. J. Hepatology 2017; 66:1300-1312) but face a variety of challenges due to the complex nature of macrophage functions and interactions in the disease state. Moreover, macrophage subsets can perform quite opposing functions suggesting that the specific properties of macrophages to be administered, as well as their optimal dosing and timing need to be carefully considered and established for any therapeutic intervention.

SUMMARY OF THE INVENTION

Administration of unpolarised monocyte-derived mature macrophages in humans and their effect in the treatment of liver cirrhosis has not been previously assessed to date.

Accordingly, in a first aspect the invention provides autologous isolated unpolarized human macrophages for use in the treatment of liver disease.

In some embodiments the unpolarized human macrophages for use in accordance with any aspect or embodiment of the invention are monocyte-derived. In some embodiments the unpolarized human macrophages for use in accordance with any aspect or embodiment of the invention are mature macrophages. Suitably, the macrophages for use in accordance with the invention are characterised by high or elevated expression of at least one macrophage-associated surface marker such as 25F9 or CD206; in some embodiments, expression is "high" or "elevated" in comparison to the expression level of these markers on the precursor or source cell such as freshly-isolated peripheral blood monocytes. Other surface markers include presence and/or high expression of one or more of CD163 or CD169. In some embodiments, absence of CD93 and a decrease in the inflammatory cytokine receptor CCR2, compared to isolated CD14+ monocytes on day 0, may be detected. In particular embodiments, unpolarised macrophages are characterised by positive expression of CD45/CD14, have viability greater than 80% and have a MFI (mean fluorescence intensity) for the surface markers 25F9 and CD206 more than 5 fold higher than the MFI of the original monocytes at day 0.

In one embodiment, autologous isolated unpolarized human macrophages for use in accordance with any aspect or embodiment of the invention are prepared from CD14+ monocytes isolated from peripheral blood of a diseased patient. Suitably these CD14+ monocytes are incubated with M-CSF for at least 48 hours, or for 3 to 5 days, or 7 days. In some embodiments, M-CSF is used at a concentration of approx. 100 ng/ml although it will be appreciated that this amount may be varied to obtain unpolarized macrophages having the desired characteristics. In one embodiment, the unpolarized macrophages for use in accordance with any aspect or embodiment of the invention are obtained by or obtainable by a process as described in the Examples herein. In particular, the process is as described in Example 4A or 4B herein. In further aspects, the invention provides autologous macrophages obtained by or obtainable by a process as set out in Example 4A or 4B. In some embodiments, the monocytes are incubated in a T cell media as described herein.

In some embodiments, the autologous isolated unpolarized human macrophages in accordance with the invention are for use in liver cirrhosis, preferably wherein liver cirrhosis is caused by any of high alcohol consumption, obesity, metabolic disorders or viral infections, most preferably alcohol-induced liver cirrhosis, NASH or HCV.

In other embodiments, autologous isolated unpolarized human macrophages are for administration intravenously. Suitably the dose is from approximately $10^7$ to $10^9$ cells, suitably at least $10^7$ cells, at least $10^8$ or at least $10^9$ cells. Multiple doses may be administered.

In another aspect of the invention, there is provided macrophages for use in a method of treating fibrosis, preferably cirrhosis, by administration of one or more doses of said macrophages to a human in need thereof. In one embodiment, 1, 2, 3 or more doses of said macrophages are administered to a human in need thereof wherein there is an interval of approximately one month between each of said doses. In one embodiment, the first dose is on day 1, the second dose is on day 30 and the third dose is on day 60. In one embodiment, the macrophages are comprised in a pharmaceutical composition. In one embodiment administration of said macrophages results in a reduction in fibrosis.

In some embodiments, the human in need thereof has cirrhotic liver disease. Suitably, the human is a diseased patient having a MELD score of 10 to 16.

The number of macrophages in each dose may be varied according to the individual to be treated. In some embodiments, each dose comprises at least $1 \times 10^7$ macrophages, suitably $1 \times 10^8$ or $1 \times 10^9$ macrophages per dose.

In one embodiment, administration of each dose is by intravenous administration. Suitably, intravenous administration is via a peripheral vein.

The macrophages for use in a method in accordance with this aspect of the invention are preferably in an unpolarised state. Suitably such macrophages are characterised by high expression of 25F9 or CD206 over that seen on the monocytes from which they are derived. In some embodiments, the unpolarized macrophages are derived from the human's own PBMCs i.e. are autologous. In other embodiments, the unpolarized macrophages may be allogeneic, e.g. derived from a healthy donor for administration to a patient with a relevant disease. In other embodiments, the unpolarized macrophages may be derived from stem cells bone marrow (BM), embryonic stem cells (ESC) or induced pluripotent stem cells (iPSC). Methods for generating suitable macrophages are described herein.

In another aspect, the invention provides autologous macrophages for use in a method of treating cirrhosis by intravenous administration of 3 doses of up to $10^9$ cells to a human having a MELD score of 10 to 16. Suitably these doses are provided approximately one month apart or at approximately 30 day intervals. In some embodiments, a use comprising autologous macrophages in accordance with the invention may be combined with another agent used in the treatment of liver cirrhosis or with an anti-fibrotic agent. In some embodiments, the other agent may be G-CSF, such as recombinant human G-CSF.

Other aspects and embodiments of any aspect of the invention are set out in the following numbered clauses:

1. A method for preparing autologous isolated unpolarized human macrophages comprising:
   a) isolating monocytes from the peripheral blood of a patient, suitably a diseased human patient;
   b) incubating those isolated monocytes in media with from 50 to 150 ng/ml of M-CSF for at least 48 hours.
2. The method according to clause 1, wherein the isolated monocytes are incubated with 100 ng/mL of M-CSF.
3. The method according to clause 1 or clause 2, wherein the isolated monocytes are incubated in culture bags.
4. The method according to any of clauses 1-3, wherein the isolated monocytes are incubated with M-CSF for 7 days.
5. A method according to any of clauses 1-4 wherein the isolated monocytes are incubated at a density of $2 \times 10^6$ monocytes per cm$^2$ and per ml.
6. A method according to any of clauses 1-5 wherein the monocytes are characterised by surface expression of CD14.
7. A method according to any of clauses 1 to 6 wherein the monocytes are isolated using CD14 microbead selection.
8. A method according to any of clauses 1 to 7 wherein, after incubation with M-CSF, the autologous isolated unpolarized human macrophages are characterised by positive expression of CD45/CD14, have a viability greater than 80% and have a MFI (mean fluorescence intensity) for the surface markers 25F9 and CD206 more than 5 fold higher than the MFI of the original monocytes at day 0.
9. A method according to any of clauses 1 to 8 wherein the diseased patient has liver cirrhosis.
10. A method according to clause 9 wherein liver cirrhosis is caused by any of high alcohol consumption, obesity, a metabolic disorder or viral infection.
11. A preparation of autologous unpolarized human macrophages for administration to a diseased patient comprising:
    a) unpolarized human macrophages produced according to the method of any of clauses 1 to 10; and
    b) an excipient
       wherein:
    c) the unpolarised human macrophages exhibit high expression of at least one surface marker chosen from 25F9, CD206, CD163, CD169, or a combination thereof; and/or
    d) wherein the preparation comprises at least $1 \times 10^7$ unpolarised human macrophages; and/or
    e) wherein the preparation is formulated as an infusion for intravenous or subcutaneous administration; and/or
    f) wherein the preparation comprises less than 4.5% v/v serum.
12. A preparation according to clause 11 wherein the excipient comprises 0.9% v/v saline with 0.5% v/v human serum albumin.
13. A method of treating liver disease in a human by administration of autologous isolated unpolarized human macrophages.
14. A method according to clause 13 wherein the unpolarized human macrophages are monocyte-derived.
15. A method according to any of clauses 13 to 14 wherein the unpolarized human macrophages are characterised by elevated expression of 25F9 or CD206 over source cells.
16. A method according to any of clauses 13 to 15 wherein the unpolarized human macrophages are prepared according to a method according to any of clauses 1 to 10.
17. A method as claimed in any of clauses 13 to 16 wherein the administration is infused, preferably intravenously.
18. A method according to clause 17 wherein the infusion is via a peripheral vein.
19. A method according to any of clauses 13 to 17 wherein the administration or infusion is a dose of between $10^7$-$10^9$ cells.
20. A method according to clause 19 wherein the patient receives three infusions one month apart.
21. A method according to any of clauses 13 to 19 wherein the patient has a MELD score of 10 to 16.
22. A method for treatment of liver disease in a patient having a MELD score of 10 to 16 comprising administering a therapeutically effective amount of a) autologous macrophages prepared by a method according to any of clauses 1 to 10; and b) an anti-fibrotic agent and/or G-CSF.
23. A method for promoting liver cell regeneration in the liver comprising administering an effective amount of autologous isolated unpolarized human macrophages into a patient.
24. A method according to clause 23 wherein the administration is intravenously, preferably via a peripheral vein.
25. A method according to clause 23 or 24 wherein the patient has alcohol-induced cirrhosis.

26. A method according to any of clauses 23 to 25 wherein $10^7$ to $10^9$ autologous cells are administered per dose.

FIGURES

FIG. 1. Initial optimization of GMP macrophage culture from normal donors. A) CliniMACS CD14 bead isolation of monocytes using LS Columns generated highly purified CD14 fractions (n=26). B) CliniMACS Prodigy CD14 selection produced equally highly enriched CD14+ fractions from apheresis collection from cirrhotic volunteers. C) Cirrhotic patients showed a trend to higher CD14 numbers in peripheral blood (n=11, p=0.108). D) Though not significant, TexMACS produced the highest and most consistent yield of macrophages (n=6-10). E) Macrophages from TexMACS culture were also significantly larger in size than those cultured in AIM-V medium (p<0.0001, n=5). F) The GMP-grade M-CSF from R&D generated a similar yield of macrophages to standard M-CSF, but with stronger expression of macrophage marker 25F9 (n=6). G) Microscopic imaging indicates that DMEM+5% AB produced clumping and sticking in macrophage cultures, unlike those generated in defined media. (Fraser et al. Cytotherapy 2017; 19(9): 1113-1124).

Figure 2:
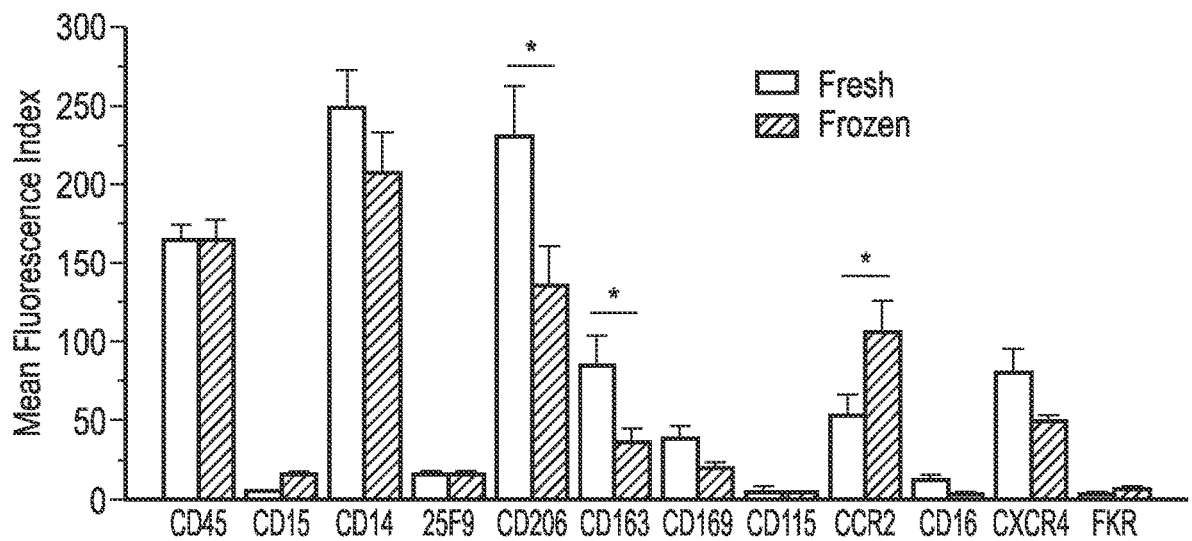

FIG. 2. Phenotyping of fresh versus frozen monocytes for GMP macrophages. Buffy coat monocytes were isolated, an aliquot frozen and stored in LN2 and the remainder used to generate macrophages. After thawing, monocytes were cultured to macrophages and phenotype compared. Although many markers are unchanged in macrophages made from thawed monocytes, CD206 and CD163 are significantly reduced and CCR2 significantly increased in macrophages from frozen monocytes (n=10).

Figure 3:
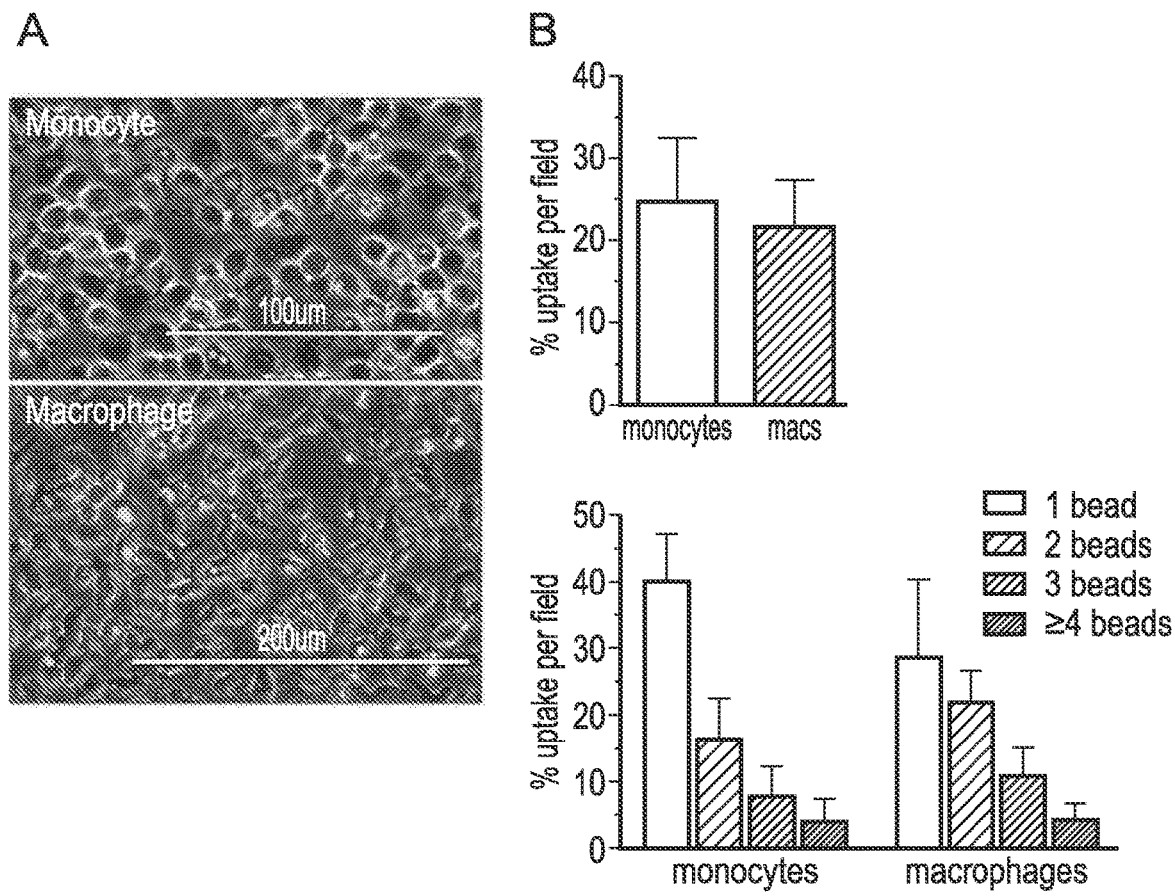

FIG. 3. Phagocytosis of monocytes and macrophages. (A) EVOS image of bright-field/fluorescein isothiocyanate fluorescence indicating pHRodo bead uptake (magnification× 100). (B) Quantification of uptake indicates that there is no significant difference in uptake of beads by monocytes or macrophages, and no difference in number of beads that were taken up (n=4). Data are expressed as mean±SD.

Figure 4:
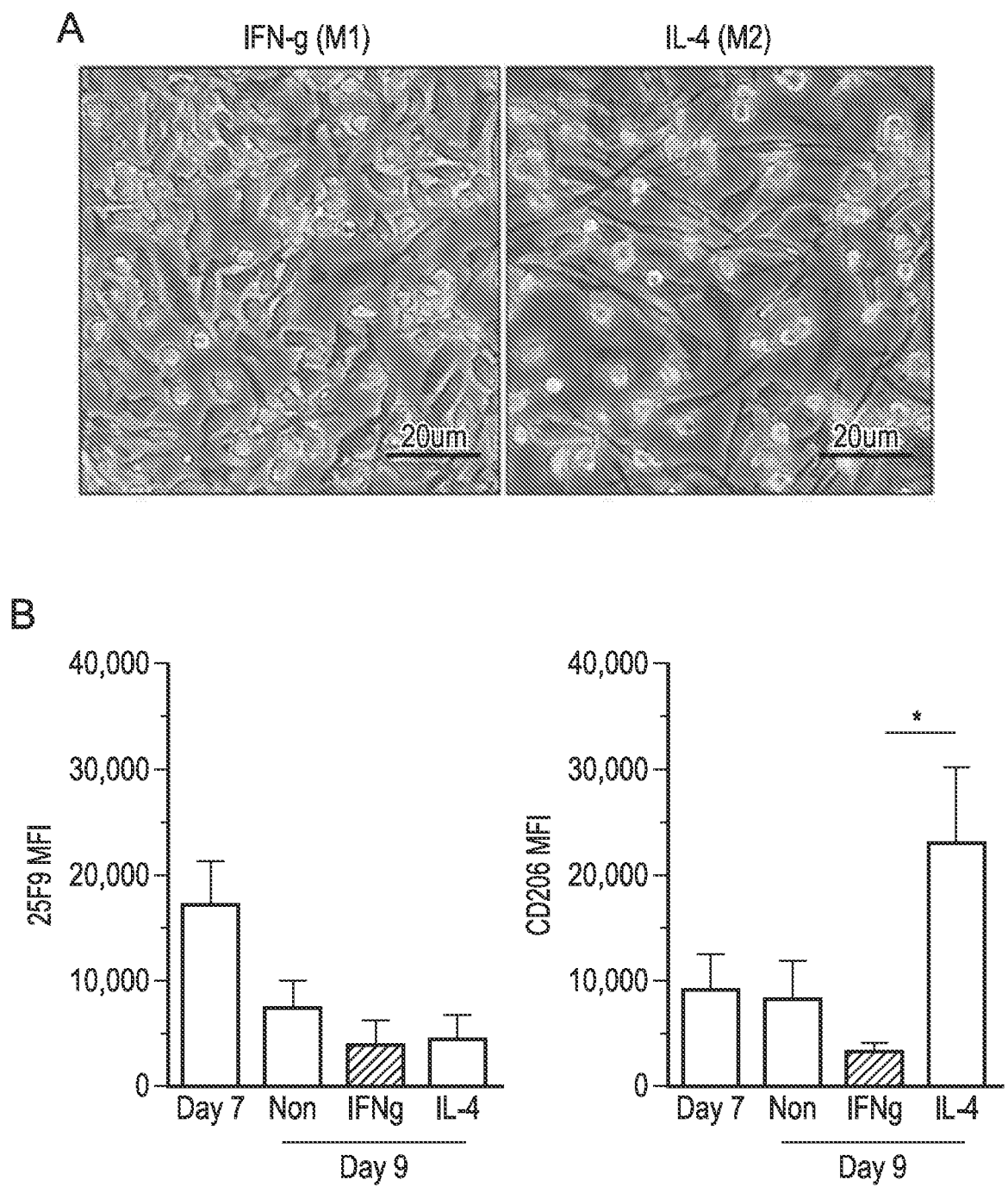

FIG. 4. Microscopic and phenotypic changes in polarized macrophages A) EVOS brightfield image of polarized macrophages showing distinct differences in morphology, with angular, spiky M1/M(IFNg) and elongated smooth spindle-shaped M2/M(IL-4) macrophages (magnification×400). B) Flow cytometric analysis shows no significant difference in macrophage marker 25F9 in all, but IL-4 stimulated macrophages significantly increase their CD206 expression, but decreased in IFN-g treated macrophages (n=5, mean+/−sd, p<0.05).

Figure 5:
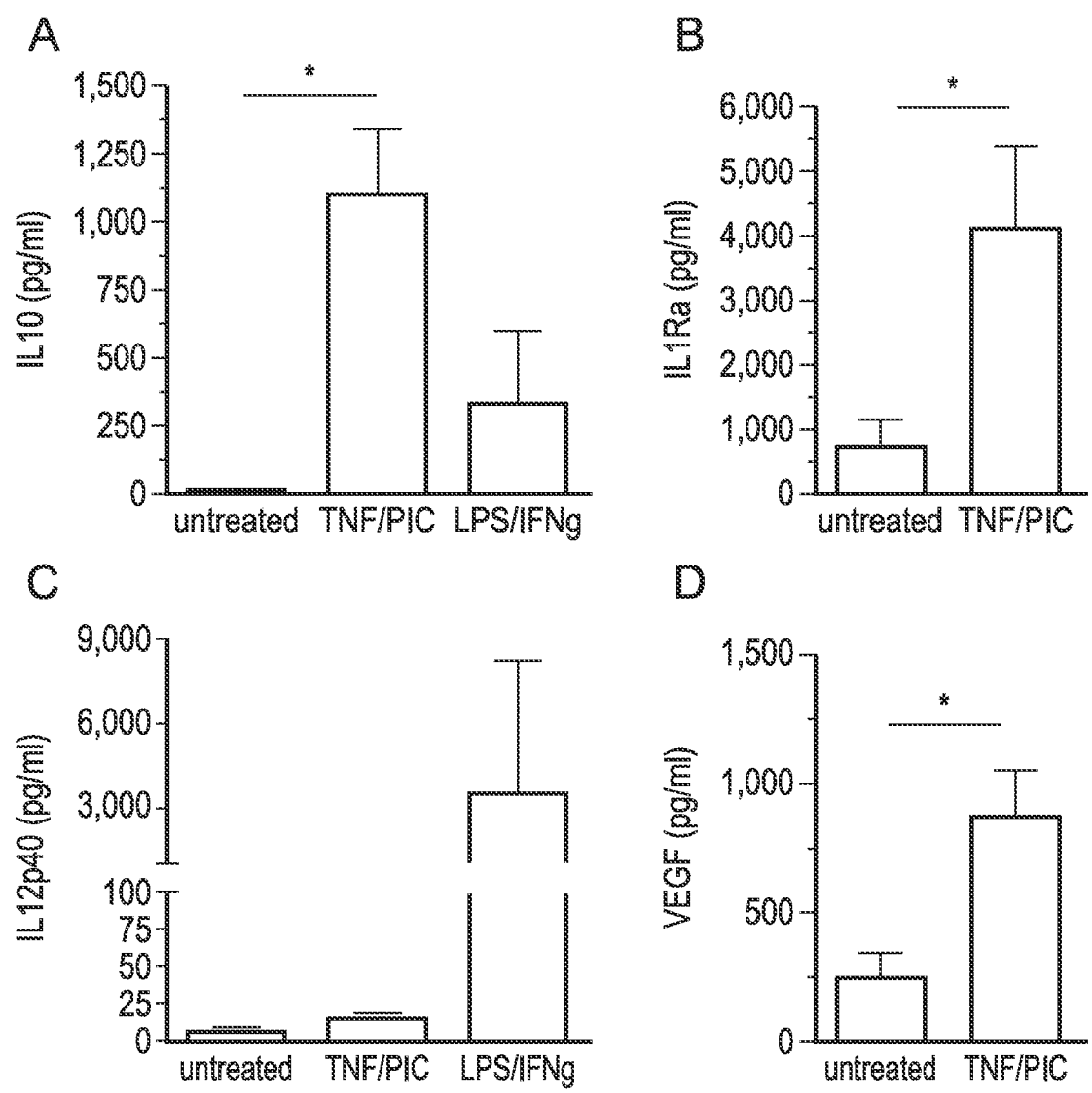

FIG. 5. Secretome analysis of healthy donor macrophages. Day 7 macrophages (n=3) were untreated or stimulated for 12 hours with TNF-α and poly I:C (PIC) or IFNg and LPS, then analysed by BioRad multiplex ELISA. Both IL-10 (A) and IL-1Ra (B) were significantly upregulated by TNF-α/PIC, as was VEGF (D). The IL-12p40 level (C) was not affected by TNF-α/PIC but was significantly increased by LPS/IFN-g. Data is expressed as mean+sd, *p<0.05.

Figure 6:
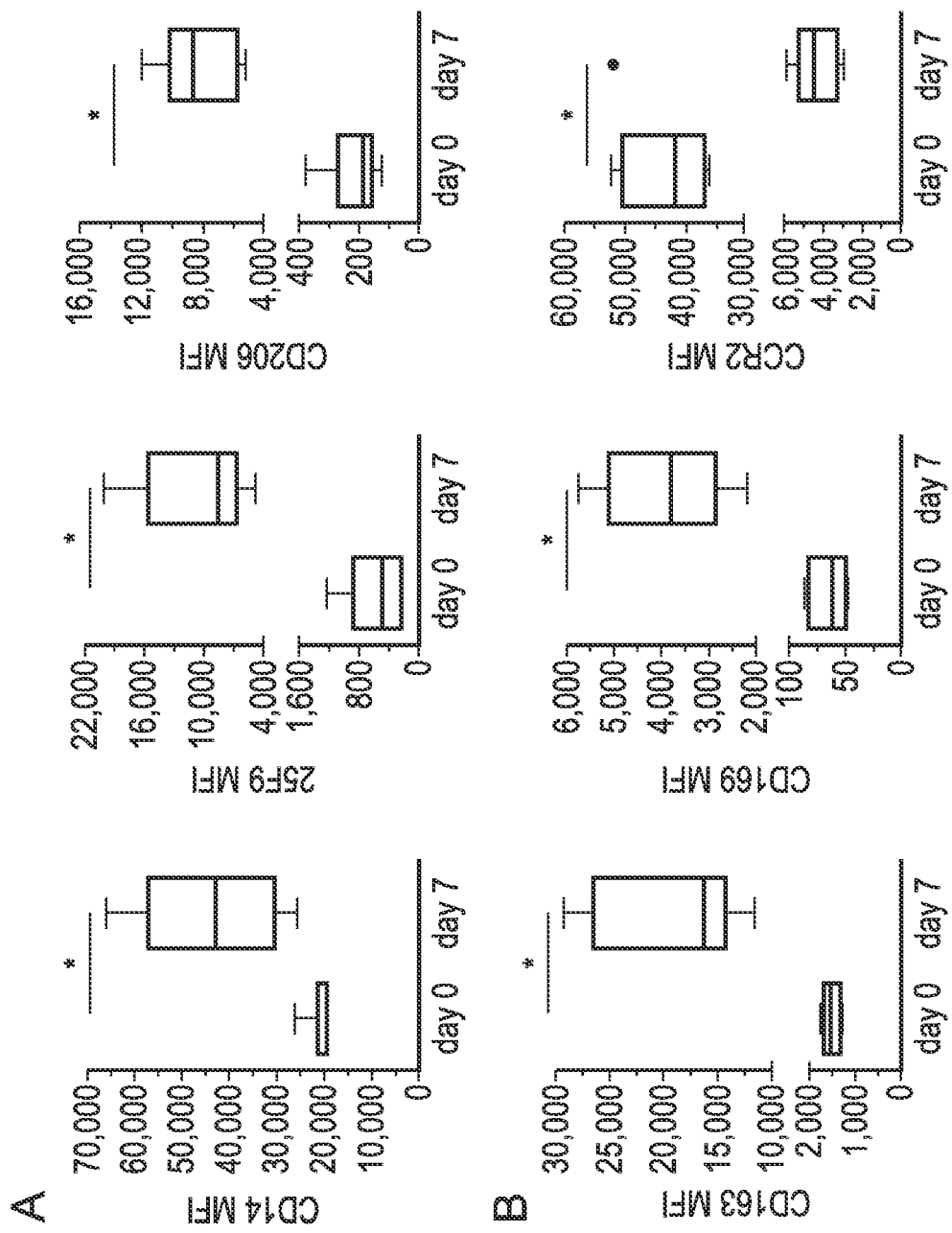

FIG. 6. Phenotype panels for clinical grade macrophages taken from cirrhotic patients (n=7). A) Release criteria showing MFI increase between day 0 monocytes and day 7 macrophages. B) Extended panel including two further scavenger receptors (CD163/CD169) plus a marker for macrophage migration. Note that there was a single outlier on the CCR2 day 7 data which was excluded from analysis after Grubb's test (•). Data is presented as mean+/−, p<0.05.

Figure 7:
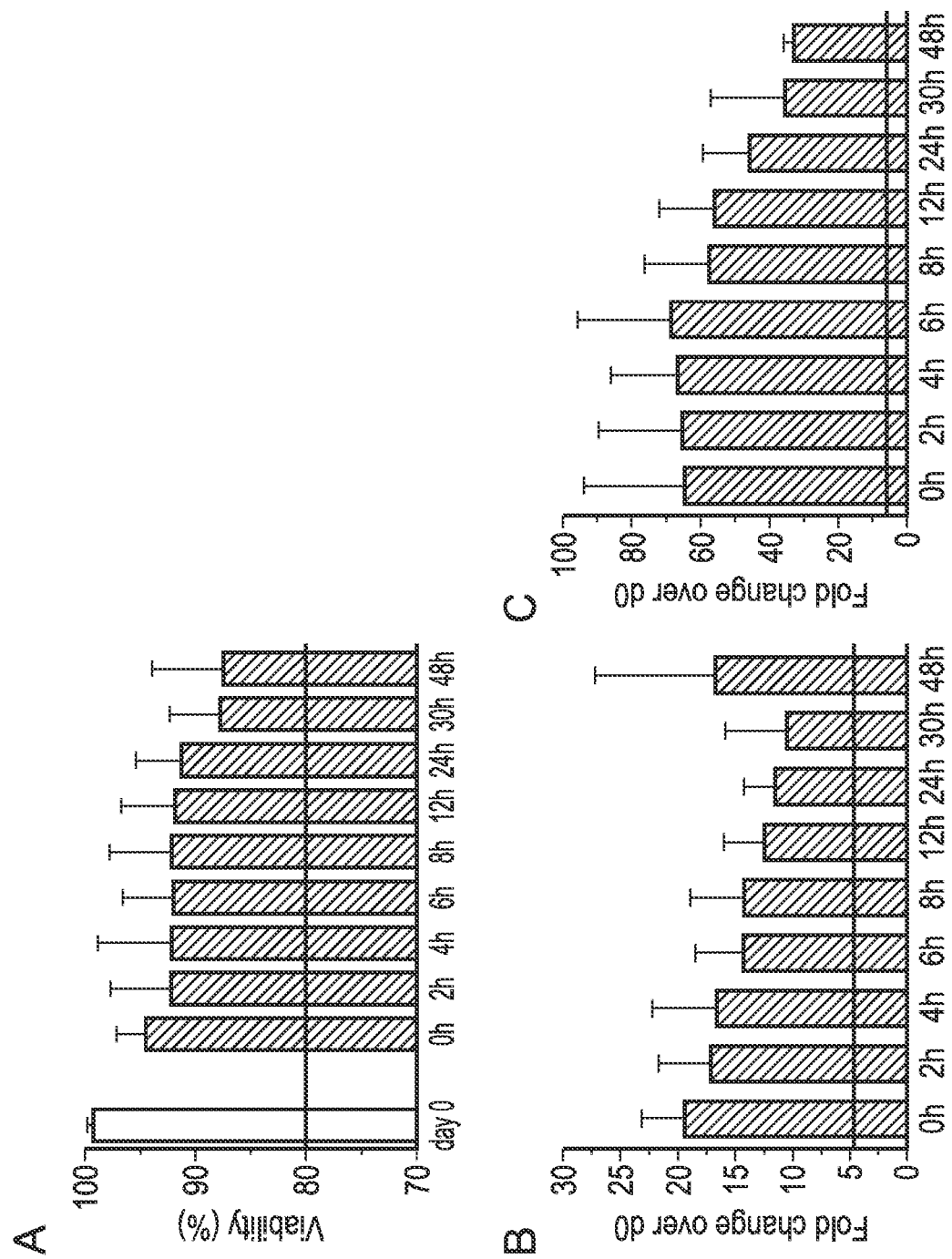

FIG. 7. Stability of GMP cirrhotic patient macrophages. A) viability shows no significant decrease even after 48 hours at ambient temperature. B) Expression of 25F9 decreases steadily over time, but even at 48 hours remains well above the 5 fold increase required for validity. C) CD206 remains high till approximately 24-30 hours after harvest then drops more rapidly, but also remains well above the 5 fold threshold established for the trial criteria (n=3).

Figure 8:
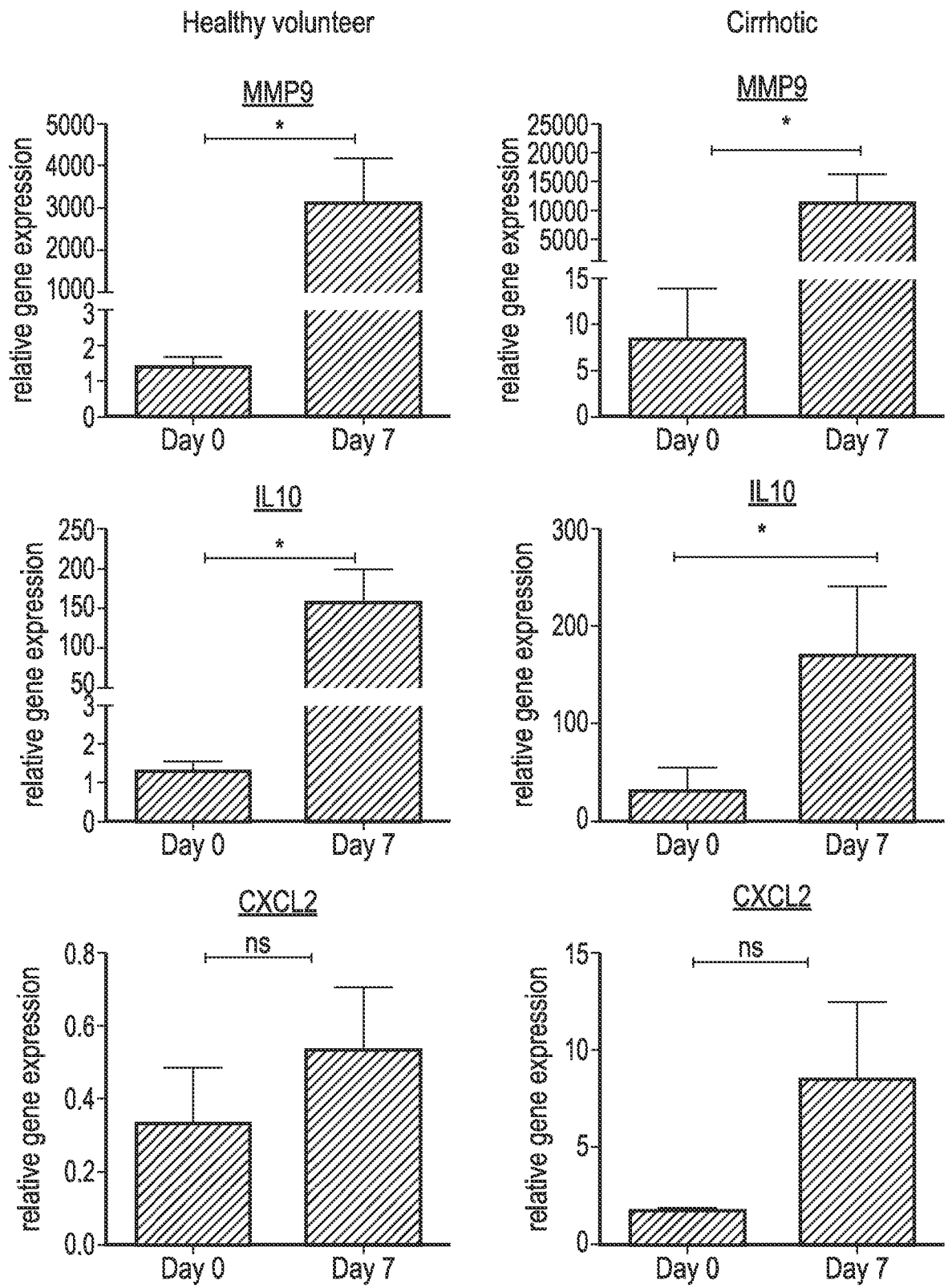
Figure 8:
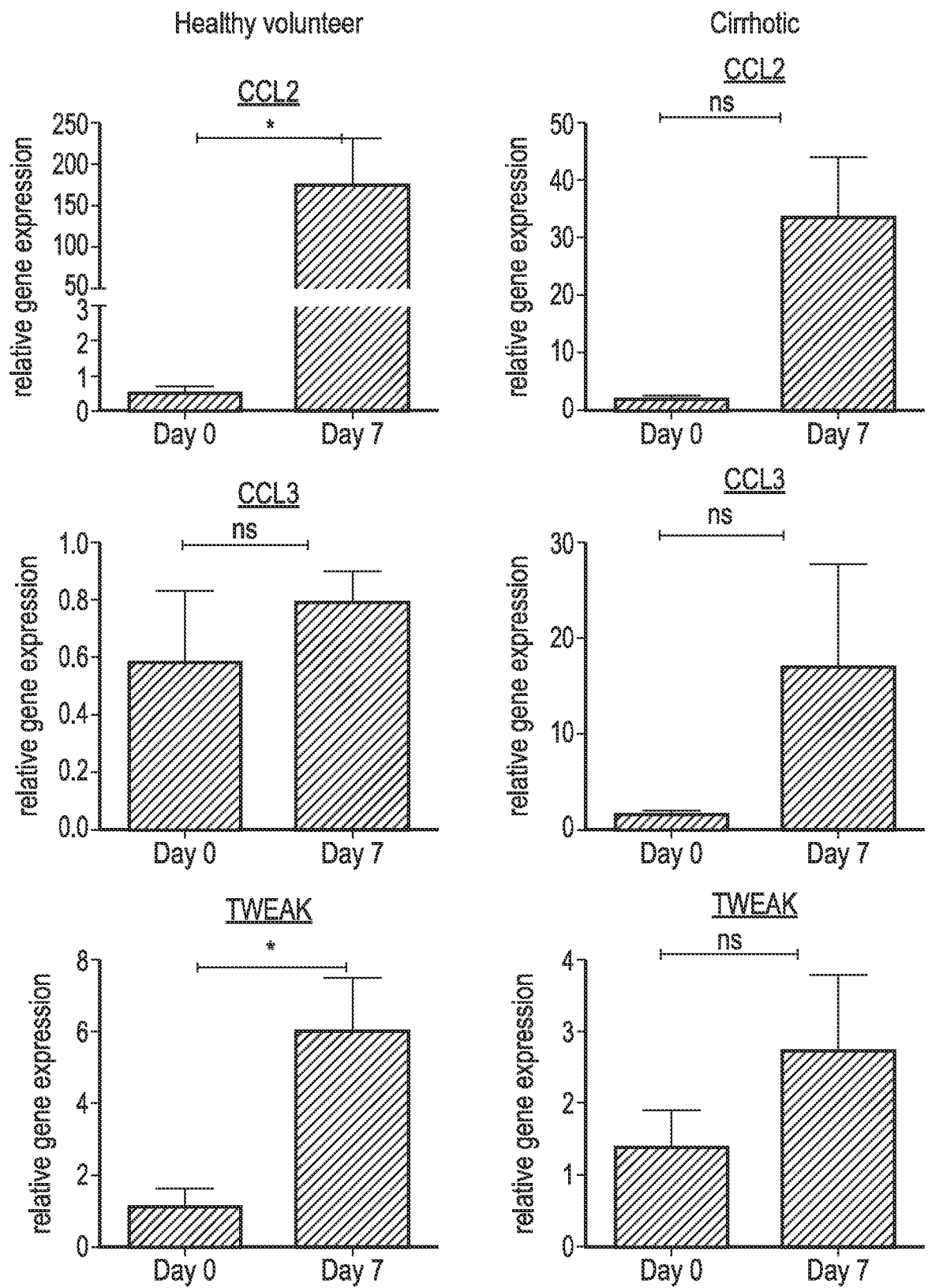

FIG. 8. Gene change between day 0 apheresis derived monocytes and after 7 days of differentiation in healthy volunteers (n=5) and cirrhotic patients (n=8), (ns, nonsignificant, *P<0.05, mean and SEM). (Moore J K et al. Cytotherapy. 2015; 17(11):1604-16)

Figure 9:
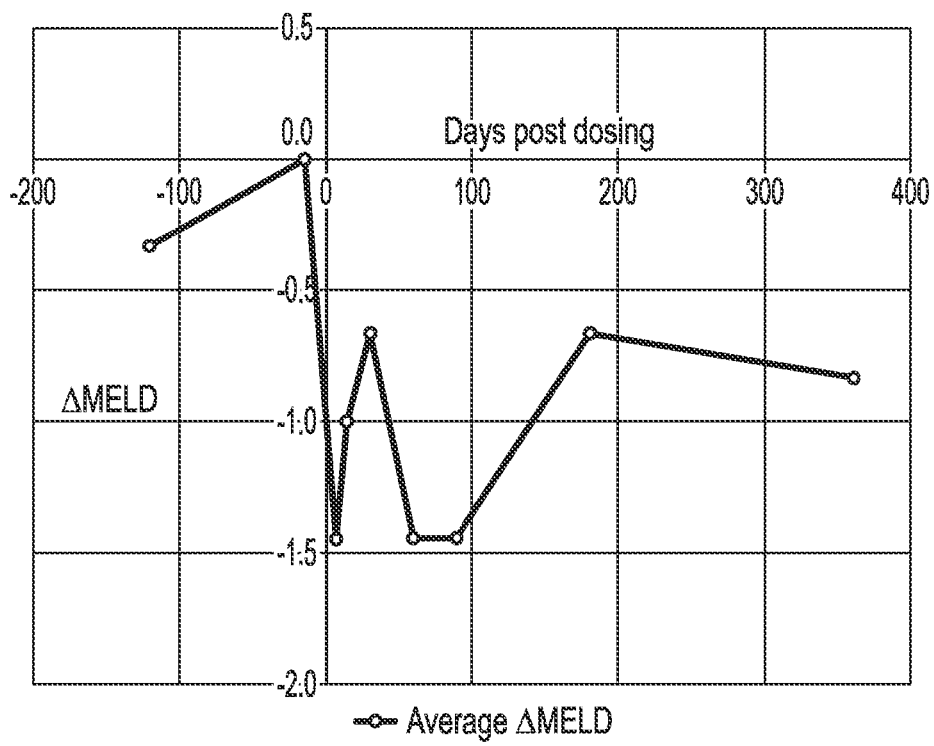

FIG. 9. The average ΔMELD for all patients in the MATCH study. d360 data from patients 9, 10 and 11 is not included.

Figure 10:
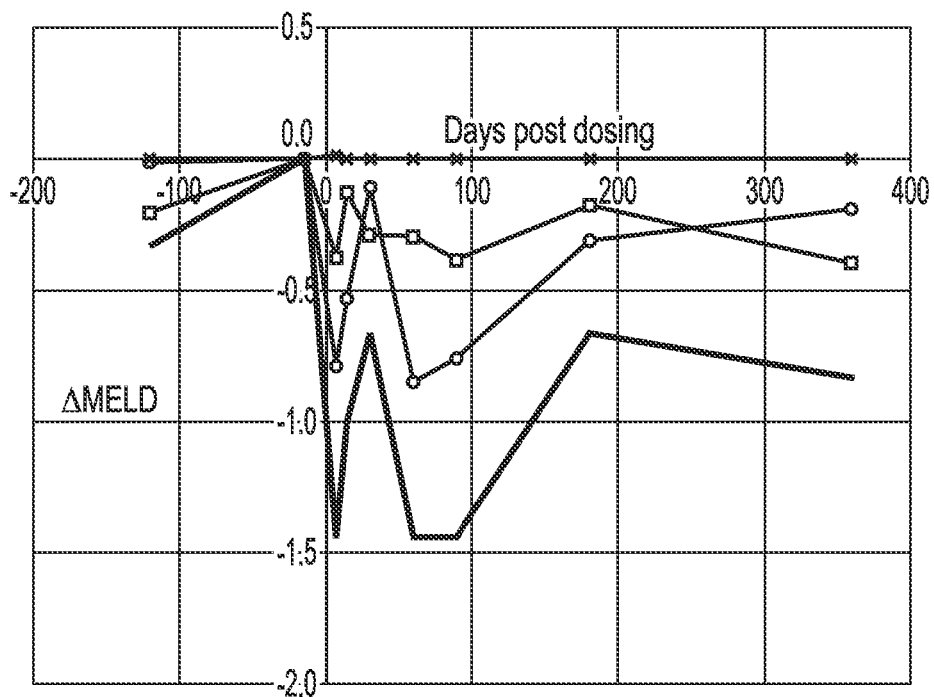

FIG. 10. The average ΔMELD for the MATCH patients, and the contributions of the 3 components; BIL, CRE and INR. d360 data from patients 9, 10 and 11 is not included.

Figure 11:
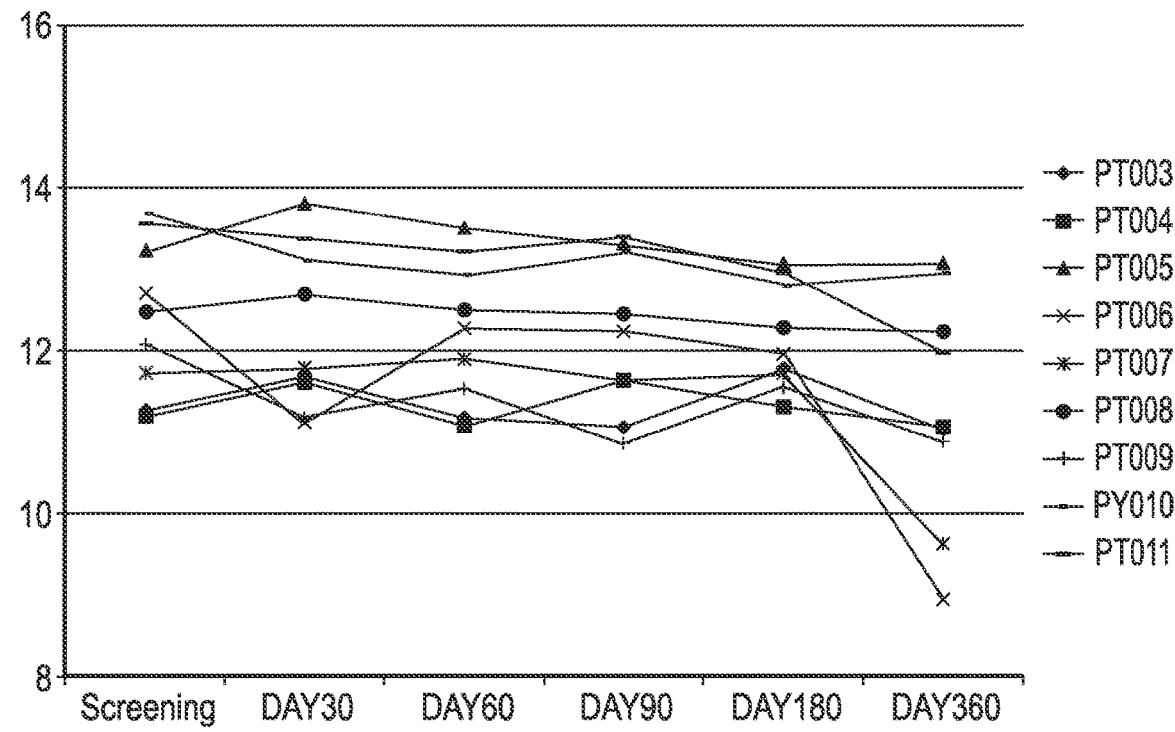

FIG. 11. The ELF score for all patients in the MATCH study.

Figure 12:
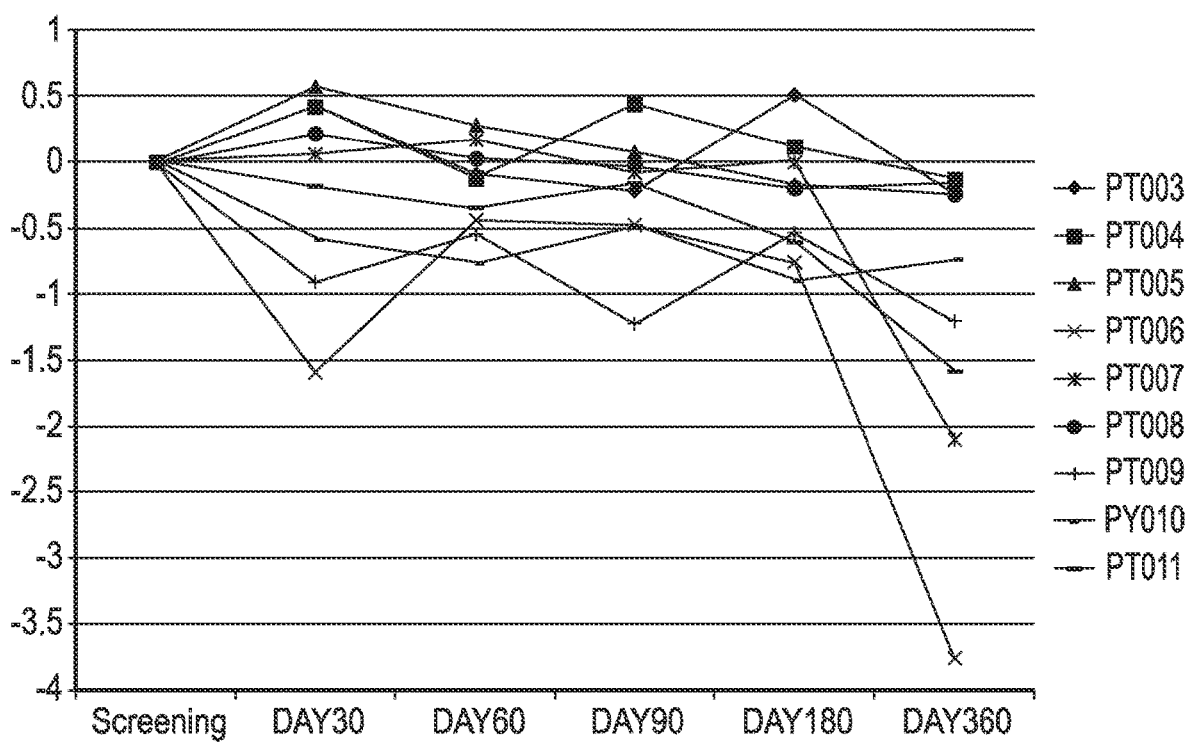

FIG. 12. The ΔELF for all patients in the MATCH study.

Figure 13:
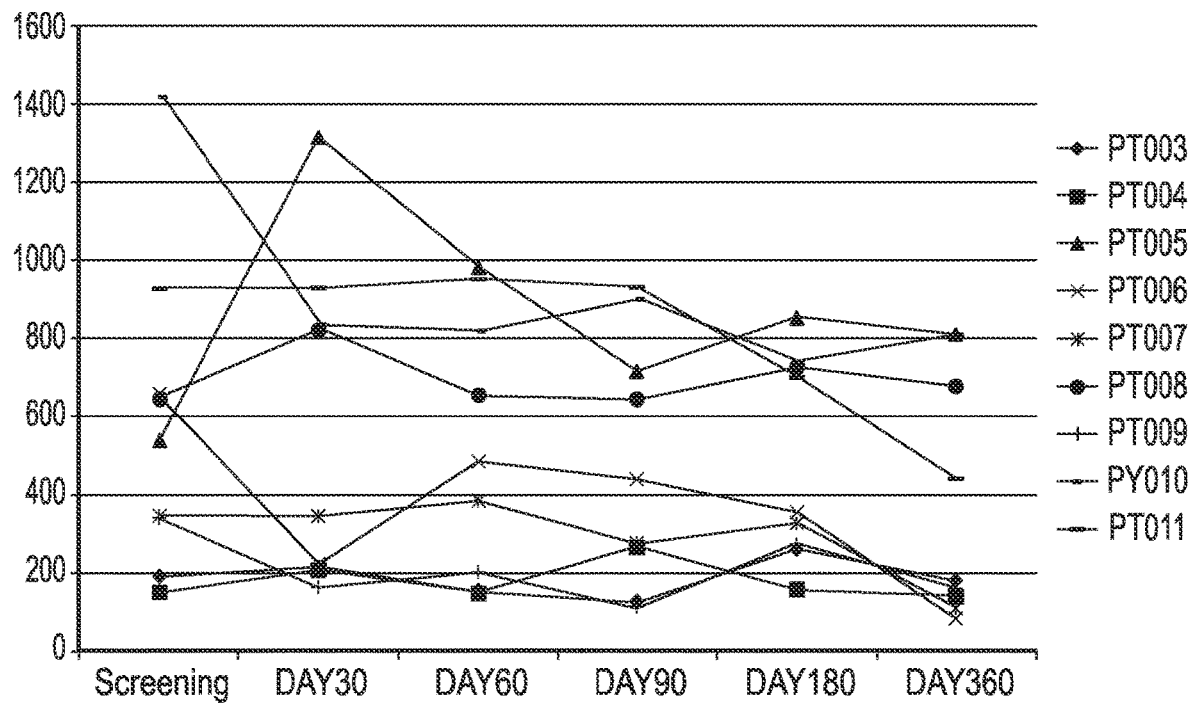

FIG. 13. The HA values for all patients in the MATCH study.

Figure 14:
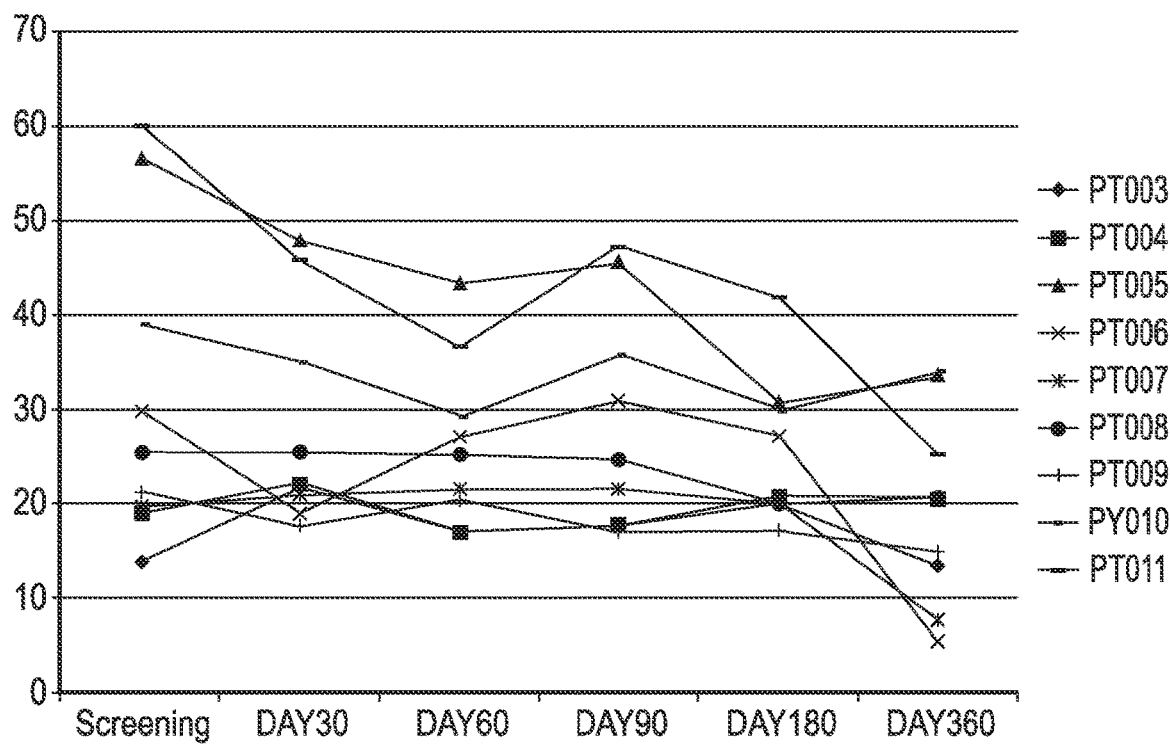

FIG. 14. The PNIIIP values for all patients in the MATCH study.

Figure 15:
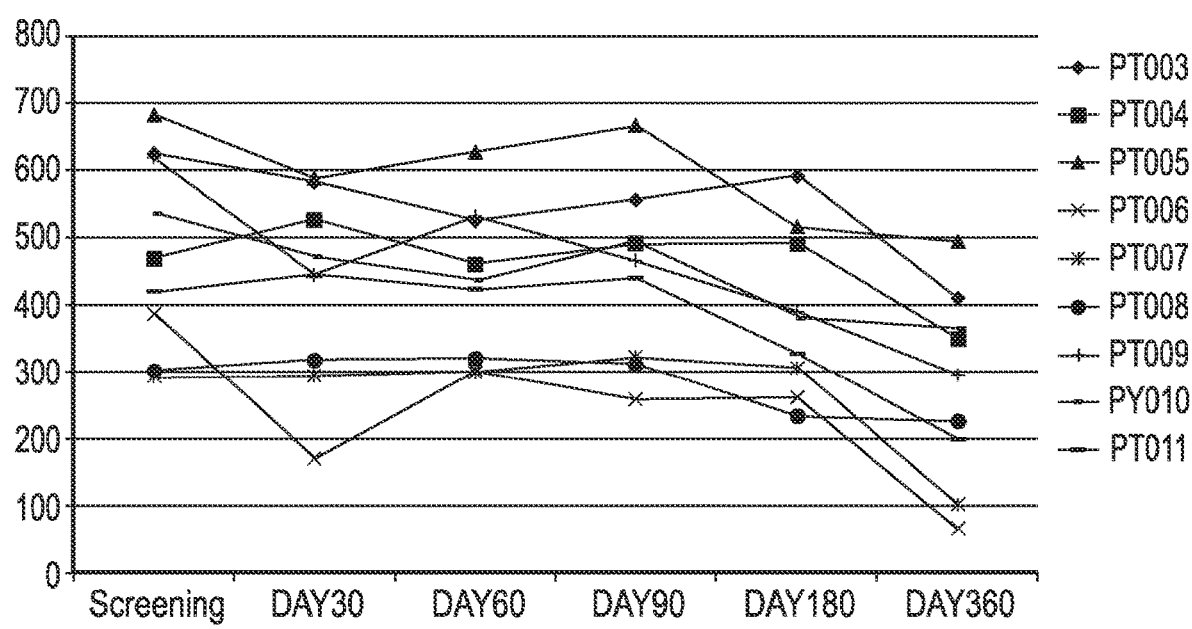

FIG. 15. The TIMP1 values for all patients in the MATCH study.

DETAILED DESCRIPTION OF THE INVENTION

Macrophages

Macrophages are phagocytic cells which have two distinct derivations—tissue resident macrophages which are derived from foetal cells, and found distributed throughout all tissues in the body, and peripheral blood monocyte-derived macrophages, which can differentiate in response to signals such as injury, inflammation and disease. Monocyte-derived macrophages have a spectrum of functions dependent upon context, and are involved in control of infectious organisms, clearance of damaged cells and repair of tissues. Early categorization of macrophages into M1 (classically-activated, inflammatory) and M2 (alternatively-activated, anti-inflammatory) is through to be an over-simplification, and macrophages can have both inflammatory and pro-resolution functions depending upon activation method and cytokine milieu, as described for example in Murray et al. (Immunity 2014; 41:14-20)) and Tacke et al. (J. Hepatology 2017; 66:1300-1312).

In the liver, macrophages can promote fibrogenesis both by activating the pro-fibrotic cytokine Transforming Growth Factor (TGF)-beta and by stimulating myofibroblast proliferation via platelet-derived growth factor (PDGF), IL-1beta and tumor necrosis factor-alpha. They are also critical for fibrosis resolution because they provide a rich source of the scar-degrading matrix metalloproteinases (MMPs). They produce factors such as MMP-9, which promote hepatic stellate cell apoptosis, needed for scar resolution. They also phagocytose cellular debris, which removes potential pro-inflammatory signals. The wide variety of responses is reviewed, for example by Tacke et al. (J. Hepatology 2017; 66: 1300-1312).

Cirrhotic donors have high numbers of circulating monocytes, commonly >30% of the total nucleated cells (TNC) which is considerably more than reported values for healthy donors or the patients donating for CD14 processing (Campbell et al. Methods Mol Med. 2005; 109:55-70) and there is a close association with this and disease progression (Zimmermann et al. PLoS One 2010; 5(6):e11049). However, it has not previously been established that monocytes isolated from cirrhotic patients will be able to differentiate into functional macrophages comparable to those from healthy volunteers. The data presented herein reports no significant changes between the functionality of macrophages derived from cirrhotic patients and healthy volunteers which indicates that the ex vivo maturation of circulating monocytes can be a technique to produce therapeutic mature macrophages for clinical cell therapy. Advantageously therefor a use of autologous cells i.e. the cirrhotic patient's own cells, is provided which minimises the risks of bio-incompatibility and immunological reactions from cell therapy. In addition, very high starting numbers of target cells can potentially reduce overall selection efficiency due to overwhelming the capacity of reagent and selection columns. Despite the high monocyte numbers in cirrhotic patients, the CliniMACS Prodigy system was surprisingly able to reproducibly isolate sufficient cells to meet a manufacturing criteria of a yield of at least 40% CD14+ cells.

As described herein, the monocytes are cultured in GMP compliant, antibiotic-free defined media generating approximately 45% conversion rate to macrophages. The culture conditions are different to previous prior art.

Unpolarized Macrophages

Suitably, "unpolarized macrophages" in accordance with the invention are mature macrophages (i.e. have fully differentiated from the source macrophage progenitor or precursor cells, such as monocytes) but unpolarized (i.e. have not received further stimulation to induce a particular functional capacity). Unpolarized macrophages may also be described as "naïve" or "non-activated".

In one embodiment of any aspect of the invention, unpolarized macrophages are monocyte-derived cells. Thus, unpolarized macrophages may be derived from peripheral blood mononuclear cells (PBMCs) removed, for example, by leukapheresis or from a blood sample, and through isolating and culturing mononuclear cells. Suitably, monocytes cells are CD14+ cells which can be isolated through selecting for CD14 expression. Suitable methods are described herein and may include magnetic microbead selection.

In some embodiments, the PBMCs are removed from the patient to be treated so as to obtain patient-derived monocytes from which autologous unpolarized macrophage can be generated. Suitable methods for removing PBMCs from patients are described, for example, herein. Advantageously using autologous cells may avoid problems encountered from non-autologous approaches such as the introduction of exogenous bacteria or viruses, bio-incompatibility and immune rejection. In other embodiments, unpolarized macrophages may be allogeneic i.e. derived from monocytes obtained from a healthy donor. Suitably the healthy donor is matched, for example matched for HLA type. Briefly, methods for generating unpolarized macrophages include culturing CD14+ monocytes isolated from PBMCs in the presence of M-CSF to generate mature macrophages. Suitably, the isolated monocytes may be incubated for at least 48 hours or more, such as 3 or more days, preferably 7 days. In some embodiments, the patient-derived PBMCs may be maintained for a period e.g. overnight before processing or culturing to produce mature unpolarized macrophages. In some embodiments, those isolated cells may be provided in culture bags.

In some embodiments, unpolarized macrophages are generated from patient-derived monocytes in accordance with the culture methods and conditions as described in the Examples section herein. In some embodiments, the culture media is any media suitable for generating those unpolarized macrophages from source cells. The media may be serum-free. Suitably the media is a chemically defined media such as Good Manufacturing Practice (GMP)-compliant defined media to which suitable concentration of M-CSF is added. In some embodiments, the M-CSF may be recombinant M-CSF, preferably recombinant human M-CSF. Advantageously and surprisingly, the media is a medium optimised for the cultivation and expansion of T cells rather than a media specifically optimised for macrophages. In one embodiment, the media is TexMACs (Miltenyi) or AIM-V (Thermofisher).

Suitably, the concentration of M-CSF is from 50 to 150 ng/ml, such as 100 ng/ml. In some embodiments, the method for preparing autologous unpolarized macrophages generates a population of unpolarized macrophages having a viability of greater than 80% wherein viability may be measured by methods familiar to those skilled in the art such as DRAQ7 staining as described herein.

Suitably unpolarised mature macrophages are characterised by an elevated expression of at least one or both surface markers "25F9" and CD206. By "elevated" expression is meant expression which is increased in comparison to the expression of these markers in the source macrophage progenitor or precursor cells, such as monocytes (e.g. isolated day 0/untreated monocytes). In some embodiments, "elevated" expression means expression of surface markers that is at least approximately five-fold when compared with the source cells. Expression of markers can be determined by methods known to those skilled in the art including fluorescent labelling techniques as described herein. Suitably levels or expression may be measured by Mean Fluorescence Intensity (MFI) using methods as described herein. 25F9 refers to a macrophage marker antibody supplied by eBioscience/Thermofisher, which recognises a marker on mature macrophages but not immature macrophages or monocytes, or any other blood cell. The marker to which the antibody binds is unknown; the name derives from the antibody clone. Further details are given here (https://www-.thermofisher.com/antibody/product/Mature-Macrophage-Marker-Antibody-clone-eBio25F9-25F9-Monoclonal/50-0115-41). In some embodiments, labels such as antibodies which compete with 25F9 for binding to the same surface marker may also be used to identify an unpolarized macrophage phenotype. As used herein, "expression of 25F9" means expression of the marker to which 25F9 binds.

In some embodiments, the source monocytes are $CD45^+$, $CD14^+$, $25F9^-$, $CD206^-$. Incubation in a suitable media, such as a media containing M-CSF, generates unpolarized mature macrophages which are $CD45^+$, $CD14^+$, $25F9^+$, $CD206^+$. In further embodiments, those source monocytes are also characterised by $CCR2^{high}$, $CD163^{low}$, $CD169^{low}$, maturing to unpolarized macrophages characterised by $CCR2^{mid}$, $CD163^+$, $CD169^+$.

Other markers whose expression may be increased in "unpolarized macrophages" include elevated levels of CD163 and CD 169, and reduced levels of CCR2. In some embodiments unpolarized macrophages may be described as pro-resolution and/or anti-fibrotic by virtue of the expression of particular surface markers or scavenger receptors involved in clearance and uptake of damaged cells, fibrotic material and pro-inflammatory cytokines. Nomenclature of macrophages is reviewed, for example, in Martinez and Gordon (F1000Prime Rep. 2014; 6: 13)

In some embodiments, unpolarized mature macrophages may be capable of being polarised into a M1 or M2-like phenotype by incubation with suitable polarising factors, for example M1 polarisation may be obtained by incubation with INF-gamma or TLR agonists such as LPS or poly(I:C), while M2 polarisation may be obtained by stimulating with IL4.

Unpolarized mature macrophages may also be derived from stem cells including embryonic stem cells (ES cells), human induced pluripotent stem cells (human iPSCs) and bone marrow-derived hematopoietic stem cells.

Various methods of producing macrophages from pluripotent stem cells such as ES cells and iPSCs are known in the art, see van Wilgenburg et al. (PLoS One 2013; 8(8): e71098), for example. Methods for determining that a developed cell line is pluripotent and have a normal karyotype are described, for example in Yang et al. (Stem Cells 2017; 35(4):886-897). A suitable human induced pluripotent stem cell line includes SFCi55, described, for example in co-pending application PCT/GB2017/052769.

Suitable methods of generating macrophage progenitors from such a human iPS cell line may be as follows: They were maintained in StemPro medium prepared by supplementing DMEM/F12 with Glutamax (Invitrogen) with StemPro supplement (Invitrogen), 1.8% BSA (Invitrogen), 0.1 mM β-mercaptoethanol (Invitrogen) and 20 ng/ml human basic FGF (Invitrogen). The method for differentiation of iPSCs to macrophages was adapted from van Wilgenburg et al. On Day 0, spent medium was removed from one confluent well of a 6-well plate, and replaced with 2 ml StemPro (ThermoFisher) supplemented with cytokine Mix 1 (50 ng/ml BMP4, 50 ng/ml VEGF, and 20 ng/ml SCF). Cells were cut using the EZPassage™ tool, and gently dislodged with a Pasteur pipette. 5 They were divided equally into two wells of an Ultra-Low Attachment 6-well plate (Corning), and 2 ml X-VIVO™ 15 media with cytokine Mix 1 was added to each well. Cells were cultured in suspension for 3 days (with a cytokine top up on Day 2), to make embryoid bodies (EBs). On Day 4, EBs were lifted and transferred to gelatin-coated tissue-culture grade 6-well plates in X-VIVO™ 15 media supplemented with cytokine Mix 2 (100 ng/ml M-CSF, 25 ng/ml IL3, 2 mM Glutamax, 1% Penicillin/Streptomycin, 0.055 M β-mercaptoethanol). Approximately 30 EBs were plated in each well. EBs were maintained in this medium for the remaining duration of the protocol, with spent medium being replaced with fresh medium every 3-4 days. After about 2 weeks, the EBs produced macrophage progenitors in the culture supernatant and these were harvested and transferred to 10 cm2 bacteriological dishes in X-VIVO™ 15 medium supplemented with cytokine Mix 3 (100 ng/ml M-CSF, 2 mM Glutamax, 1% Penicillin/Streptomycin) and allowed to mature for 5-7 days into iPSC-derived macrophages (iPSC-DM). Macrophage progenitors could be harvested twice a week for approximately 2 months.

Other methods for generating macrophage progenitors are described in Yeung et al. Sci. Rep. 2015; 5: 8908, Zhuang et al. J Immunol Methods. 2012; 385 (1-2):1-14, Sneju et al. Oncoimmunology 2014; 3(1): e27927, Hale et al. PLoS One 2015; 10(5): e0124307, Zhang et al. Circ Res. 2015; 117 (1):17-28, Mucci et al. Stem Cell Reports 2016; 7(2):292-305 and van Wilgenburg et al. PLoS One 2013; 8(8): e71098.

ES cell derived macrophages (ESDMs) may be generated by culturing the ES cells in the presence of colony stimulating factor-1 (CSF-1) (also known as M-CSF) and IL-3 to form embryoid bodies (EB). Whilst EBs adhere to tissue culture plastic, macrophage progenitor cells are non-adherent and thus are released into the medium. The macrophage progenitor cells may then be harvested at various time points, for example after 10 or 20 days and plated onto non-treated Petri dishes and cultured in the presence of CSF-1 alone. This process can give rise to monocyte-like cells that adhere to the plastic forming a monolayer and mature into ESDM.

The maturation of the ES cells into ESDM can be monitored by detecting the presence of mature macrophage specific markers including 25F9 (human macrophage specific) and/or CD1 1b. Additionally, human macrophages may be characterised by the absence of the monocyte marker CD93. Advantageously, the method described yields a substantially homogenous population of ESDM.

Liver Diseases

In some aspects or embodiments the invention provides for treatment of a liver disease in a patient, in particular a patient that has suffered liver injury leading to liver fibrosis or cirrhosis. Chronic liver injury results in scar deposition and hepatocyte loss. Excessive accumulation of scar tissue results in liver fibrosis. At this stage, fibrosis can be reversed. However, untreated fibrosis can ultimately lead to cirrhosis. In some embodiments, the liver disease is one in which cirrhosis is caused by damage to hepatocytes, for example, is a hepatocyte-derived disease, such as those diseases of viral origin (including treated (sustained viral response) hepatitis C (HCV), hepatitis B), damage through alcoholism (alcohol related liver disease (ALD)), or non-alcoholic fatty liver disease (NAFLD), including Non-alcoholic steatohepatitis (NASH) (including NASH resulting from diabetes or obesity), cryptogenic cirrhosis, hemochromatosis or alpha-1-antitrypsin deficiency. In some embodiments, the underlying aetiology has been removed (for example, a patient suffering from damage through alcoholism is no longer drinking, or a patient suffering from damage through HCV no longer has HCV etc.).

A diseased patient suitable for a treatment or use in accordance with any aspect or embodiment of the invention may be a patient with a relevant disease and severity.

Treatment

The term "treatment" as used herein refers to an intervention which reduces fibrosis, prevents the progression, or reduces partially or completely the clinical symptoms with a liver disease or injury in a subject. Suitably, the treatment may result in an increase in or an acceleration of liver regeneration. Advantageously, the macrophages used in accordance with the invention provide anti-fibrotic and pro-regenerative cells.

Suitably, administration of unpolarized human macrophages in accordance with the invention may result in one of more of the following advantageous effects: a reduction in fibrosis or a reduction in liver disease in an subject, a reduction in necrosis, an increase in liver cell proliferation, a reduction in levels of pro-inflammatory cytokines, an increase in phagocytosis at the site of fibrosis.

Typically, liver disease is measured by the MELD (Measure of End-stage Liver Disease) score, a scoring system derived from serum markers blood bilirubin, creatinine and clotting potential. The scale was originally developed to predict mortality and is used to prioritize patients for liver transplantation. It predicts three month and one year mortality and predicts clinical decompensation in patients with compensated cirrhosis.

A change in MELD is a more significant determinant of death than initial MELD alone. For any given MELD, the magnitude and direction of change in MELD score during the previous 30 days is a significant independent mortality predictor. MELD score has been used by all the major Western regulatory authorities involved in liver transplantation (UK Transplant, Eurotransplant and LINOS) to help prioritise the allocation of liver transplants. In some embodiments, treatment with unpolarized human macrophages in accordance with the invention may result in a change in the MELD in a subject. In other embodiments, treatment may result in a change in one of the liver-related components of the MELD score i.e. bilirubin (BIL) and/or international normalized ratio (INR).

In other embodiments, treatment with unpolarized human macrophages in accordance with the invention may result in a change in UKELD. Other methods for measuring an effect in a subject include assessing changes in liver fibrosis as measured by transient elastography, by using an Enhanced Liver Fibrosis Test)—ELISA, by measuring liver metabolism and regenerative activity using labelled metabolites and a liver MRI scan or measuring liver volume and blood flow using MRI. In other embodiments, treatment with unpolarized human macrophages in accordance with the invention may result in a change of ELF or one of the liver-related components of ELF score i.e. hyaluronic acid (HA), tissue inhibitor of metalloproteinase-1 (TIMP-1) and propeptide of type III procollagen (PIIINP), In other embodiments, disease specific biomarkers and epitopes such as neoepitopes may be measured. For example, treatment with unpolarized human macrophages in accordance with the invention may result in a change in the precisely cleaved N-terminal propeptide of type III collagen (PRO-C3) and/or a peptide of helical collagen type III degradation (C3M). During fibrillar assembly the N-terminal propeptide of type III collagen is cleaved off by N-proteases but sometimes the removal of the propeptide is incomplete, thus PIIINP can be a marker of both fibrillogenesis formation and degradation, whereas PRO-C3 is a marker of formation as PRO-C3 is specific to the N-protease cleavage site. For example, ELF, liver related components of ELF, PRO-C3 and C3M may be measured in accordance with any of the following documents: Thiele et al. (Gastroenterology 2018; 154: 1369-1379), Irvine K et al. (Liver International 2016, 370-377 ISSN 1478-3223), Barascuk N et al. (Clinical Biochemistry 34 (2010) 899-904), and Nielsen M J et al. (Am J Transl Res 2013; 5(3): 303-315).

The term "subject" as used herein, refers to any individual who may benefit from the treatment of a liver injury. The subject may be a human subject, a human in need of a treatment, such as a diseased patient. Suitably a human suitable for a treatment in accordance with the invention is one with cirrhotic liver disease, preferably a patient having a MELD score of between 10 and 16. A human with a developing liver disease may also be suitable for such treatment, such as a human/patient with portal hypertension.

Dose

It will be appreciated that a therapeutically effective amount or dose of unpolarized macrophages will be dependent on various factors including the weight of the subject to be treated. By way of example, a therapeutically effective amount may be in the form of a dose of $1 \times 10^7$ to $1 \times 10^9$ unpolarized macrophages. In some embodiments, the dose will be multiples of $10^7$, $10^8$ or $10^9$ macrophages per dose. Suitably, the treatment will consist of three doses administered as infusions on a monthly basis i.e. 3 infusions of approximately up to $10^9$ macrophages at an interval of approximately 30 days. Advantageously, additional doses may enable further degradation of scar tissue to occur. In one embodiment, the macrophages for all doses to be administered to a patient would be collected through a single leukapheresis collection. In some embodiments, the final dose administered may depend upon the starting number of monocytes and can be multiples of $10^8$ depending upon patient.

In some embodiments, the macrophages in accordance with the invention may be provided in a suitable storage or transfer bag.

Administration

The macrophage product in accordance with any aspect of the invention can be administered into the body of the recipient by any suitable means, including but not limited to transdermally, subcutaneously, intramuscularly, parentally, enterally, intravenously, intraperitoneally, intraorbitally, intraretinally, by transplantation of tissue and into cerebrospinal fluid. Advantageously, the macrophage produce is administered intravenously such as, for example, intravenous injection or infusion.

Earlier work supports that portal vein delivery maximises the number of cells delivered to the liver, this route of delivery however, is not desirable in a clinical setting as repeated portal vein administration in cirrhosis patients risks portal hypertension and coagulopathy. The present inventors have found that although lower numbers of cells are likely to distribute to the liver following intravenous injection, this route of delivery has efficacy in the clinic.

In some embodiments, the unpolarized macrophages for use in accordance with the invention are prepared in a pharmaceutically acceptable carrier. A pharmaceutically acceptable carrier may be any substance which enables delivery of unpolarized macrophages to a subject and may include any suitable diluent or excipient or combination thereof. In some embodiments, unpolarized macrophages may be delivered in a saline solution supplemented with a human albumin solution.

Thus, the unpolarized macrophages for use in accordance with the invention may be provided in a pharmaceutical composition comprising a therapeutically effective amount of unpolarized macrophages and a pharmaceutically acceptable carrier.

In a suitable embodiment, a pharmaceutical composition of the invention may further comprise a pharmaceutically acceptable concentration of salt, buffering agents, and compatible carriers. The compositions may also include antioxidants and/or preservatives. In some embodiments a pharmaceutical composition may comprise DMSO, for example, 5-10% DMSO.

Combinations

In some embodiments, a macrophage treatment in accordance with the invention may be combined with another treatment for liver disease. Suitable treatments include treatment with G-CSF. In some embodiments, the other treatment may comprise an anti-fibrotic drug treatment. Suitable antifibrotic drugs are reviewed, for example, by Wang et al. (Front Physiol. 2016; 7: 47; doi: 10.3389/fphys.2016.00047) and Tacke et al. (J. Hepatology 2017; 66: 1300-1312)).

Various further aspects and embodiments of the present invention will be apparent to those skilled in the art in view of the present disclosure.

All documents mentioned in this specification are incorporated herein by reference in their entirety.

"and/or" where used herein is to be taken as specific disclosure of each of the two specified features or components with or without the other. For example "A and/or B"

is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

EXAMPLES

Certain aspects and embodiments of the invention will now be illustrated by way of example and with reference to the figures described above.

Example 1. Optimizing GMP-Compliant Culture of Monocytes

Isolation of Cells from Healthy Donors

Donor buffy coats as a source of healthy donor monocytes were provided by Scottish National Blood Transfusion Service (SNBTS) Blood Donor Centre, Edinburgh, United Kingdom, under SNBTS Sample Governance 13-12 and 14-02. CD14 selection from PBMCs: PBMCs were separated from normal donor buffy coats by density centrifugation using Histopaque 1077 (Sigma). After washing, CD14+ monocytes were isolated from the mononuclear cell fraction using CliniMACS GMPgrade CD14 microbeads and LS separation magnetic columns (Miltenyi Biotec). Briefly, cells were resuspended to appropriate concentration in PEA buffer (phosphate-buffered saline [PBS] plus 2.5 mmol/L ethylenediaminetetraacetic acid [EDTA] and human serum albumin [0.5% final volume of Alburex 20%, Octopharma]), incubated with CliniMACS CD14 beads per manufacturer's instructions, then washed and passed through a magnetized LS column. After washing, the purified monocytes were eluted from the demagnetized column, washed and re-suspended in relevant medium for culture.

Isolation of Cells from Cirrhotic Patients

For full-scale GMP process optimization and validation, peripheral blood mononuclear cells (PBMCs) were collected by leukapheresis in the SNBTS Clinical Apheresis Unit, Royal Infirmary of Edinburgh. Ethical approval was granted from the South East Scotland Research Ethics Committee 02. Informed consent for apheresis donation was obtained in accordance with the Helsinki Declaration. Isolation of CD14+ cells from leukapheresis: PBMCs were collected by leukapheresis from cirrhotic donors who gave informed consent to participate in the study. Eligibility criteria were age range of 18 to 75 years, and cirrhosis was defined by any one of the following: previous liver biopsy confirming histological features of cirrhosis, transient elastography (Fibroscan)>18 kPa and/or clinical and radiological features that in the opinion of the clinical lead correlated with a diagnosis of cirrhosis. For the purposes of the trial, exclusion criteria included those conditions which required ongoing anti-viral treatment such as viral hepatitis, average alcohol ingestion >21 units/week (male) or >14 units/week (female), ascites not well controlled with diuretic therapy in the preceding 3 months, encephalopathy requiring hospitalisation for treatment in the previous 3 months, portal hypertensive bleeding in the preceding 3 months, hepatocellular carcinoma, other cancer within the previous 5 years, previous liver transplant or currently on the waiting list, the presence of a clinically relevant acute illness that might compromise safe presentation and pregnancy and/or breast-feeding. Leukapheresis of peripheral blood for mononuclear cells (MNCs) was carried out using an Optia apheresis system by sterile collection. A standard collection program for MNC was used, processing 2.5 blood volumes. Isolation of CD14 cells was carried out using a GMP-compliant functionally closed system (CliniMACS Prodigy system, Miltenyi Biotec). Briefly, the leukapheresis product was sampled for cell count and an aliquot taken for pre-separation flow cytometry. The percentage of monocytes (CD14+) and absolute cell number were determined, and, if required, the volume was adjusted to meet the required criteria for selection ($\leq 20 \times 10^9$ total white blood cells; $<400 \times 10^6$ white blood cells/mL; $\leq 3.5 \times 10^9$ CD14 cells, volume 50-300 mL). CD14 cell isolation and separation was carried out using the CliniMACS Prodigy with CliniMACS CD14 microbeads (medical device class III), TS510 tubing set and LP-14 program. At the end of the process, the selected CD14+ positive monocytes were washed in PBS/EDTA buffer (CliniMACS buffer, Miltenyi) containing pharmaceutical grade 0.5% human albumin (Alburex), then re-suspended in TexMACS (or comparator) medium for culture.

Cell Count

Cell counts of total MNCs and isolated monocyte fractions were performed using a Sysmex XP-300 automated analyzer (Sysmex). Assessment of macrophage numbers was carried out by flow cytometry with TruCount tubes (Becton Dickinson) to determine absolute cell number, as the Sysmex consistently underestimated the number of macrophages. The purity of the separation was assessed using flow cytometry (FACSCanto II, BD Biosciences) with a panel of antibodies against human leukocytes (CD45-VioBlue, CD15-FITC, CD14-PE, CD16-APC), and product quality was assessed by determining the amount of neutrophil contamination (CD45int, CD15pos).

Cell Harvesting

For normal donor-derived macrophages, cells were removed from the wells at day 7 using Cell Dissociation Buffer (Gibco, Thermo Fisher) and a pastette. Cells were resuspended in PEA buffer and counted, then approximately $10^6$ cells per test were stained for flow cytometry. Leukapheresis-derived macrophages were removed from the culture bags at day 7 using PBS/EDTA buffer (CliniMACS buffer, Miltenyi) containing pharmaceutical grade 0.5% human albumin from serum (HAS; Alburex). Harvested cells were resuspended in excipient composed of two licensed products: 0.9% saline for infusion (Baxter) with 0.5% human albumin (Alburex).

Sorting Efficiency of Cells

The sorting efficiency using CD14 CliniMACS beads was extremely high, and results were comparable across all methods, whether the cells were sourced from buffy coat or leukapheresis from cirrhotic patients; bead-labelled cells were manually labelled and isolated over LS columns, or processed using the completely automated CliniMACS prodigy system. Flow cytometric analysis of the pre-sort and positive and negative fractions indicated that from an initial mean of 20.5% monocytes, the positive fraction was highly enriched (95.9%), with minimal loss in the negative fraction (4.1%) from 26 different normal donor isolates using CliniMACS CD14 reagents and LS columns (FIG. 1A). Very similar figures were seen in cirrhotic donor samples separated using the CliniMACS Prodigy (FIG. 1B), although cirrhotic donors had a higher (though not significant) initial mean percentage of monocytes in their collections (FIG. 1C).

Optimal Medium for Culturing Monocytes from Healthy Donor Samples

Optimal culture medium for macrophage differentiation was investigated, and three candidates were tested using buffy coat monocytes; Dulbecco's Modified Eagle's Medium (DMEM; Life Technologies) supplemented with 5% AB serum (SNBTS), plus two chemically defined serum-free culture media, AIM-V (Thermo Fisher) and TexMACS (Miltenyi). TexMACs medium is an optimized serum-free cell culture medium optimized for the cultivation and expansion of human and mouse T cells and regulatory T cells, containing pre-selected human serum albumin, stable glutamine, and phenol red (absent from clinical version). The experiments were carried out with buffy coat monocytes cultured in each medium for 7 days in a humidified atmosphere at 37° C. and 5% CO2 with 100 ng/mL premium grade Macrophage Colony Stimulating Factor (M-CSF, Miltenyi). Cells were seeded at a density of 1.8× 107 cells/well in 4 mL medium in six-well tissue culture plates and refed at days 3-4. The manufacture of macrophages in AIM-V complete culture medium was previously reported (Moore J K et al. Cytotherapy. 2015; 17(11):1604-16). However, the antibiotic content of this medium was not compatible with the testing of product sterility by assessment of bacterial growth and therefore the antibiotic-free TexMACS complete medium was evaluated as a comparator. GMP-grade TexMACS culture medium demonstrated a consistently higher conversion rate to macrophages compared with AIM V although this did not reach statistical significance (FIG. 1D). Culture in DMEM plus 5% AB serum also resulted in a comparable rate of macrophage conversion, however DMEM cultured macrophages were also strongly adherent to the substrate, which resulted in cell loss during harvesting (FIG. 1G). In addition, monocytes cultured in TexMACS produced significantly larger macrophages as calculated using forward scatter from flow cytometry (FIG. 1E). Initial development experiments used the previously used premium research grade M-CSF (Miltenyi) to supplement the culture medium (Moore J K et al. Cytotherapy. 2015; 17(11):1604-16). This was compared to a GMP-grade M-CSF (R&D Systems), both used at 100 ng/ml. There were no significant differences in morphology or macrophage yield when culturing with either source, but higher expression of the macrophage marker 25F9 was seen in macrophages generated with GMP-grade M-CSF (FIG. 1F). TexMACS medium (Miltenyi) supplemented with GMP-grade M-CSF (R&D Systems) was considered to be the optimal medium for the production of GMP grade macrophages.

Derivation of Macrophages from Frozen Monocytes

A comparison was also made of deriving macrophages from fresh and frozen/thawed monocytes (see Results section). Monocytes were isolated from buffy coats, then an aliquot was frozen in cryopreservation medium (Cryostor CS10, Sigma) and the remainder was cultured fresh. The frozen aliquot was thawed several days later and cultured as before.

For therapeutic use, freezing aliquots of monocytes to generate multiple macrophage doses would be attractive. It was assessed whether there were any significant differences in macrophage yield or phenotype that would preclude the use of frozen stocks. The data indicated that there were differences in both yield and in phenotype. In particular, there were significant drops in the expression of CD206 and CD163 (FIG. 2). There was also a converse increase in CCR2 expression (FIG. 2). This would suggest that the macrophages from frozen monocytes develop a more M1-like, classically activated phenotype. Additionally, the mean viability of macrophages from thawed monocytes was significantly lower than from fresh monocytes in these experiments (viability 45.5% versus 75.2% in fresh macrophages, n=4-6, P=0.0098). It was concluded that the poor viability (and therefore yields) and less advantageous phenotype precluded the further development of the macrophage product from frozen cells for initial clinical use.

Example 2. Extended Functional Analysis: Healthy Donor Macrophages

Phagocytic Uptake of Monocytes and Macrophages

Functional characterization of normal macrophages investigated the capacity of the cells to take up particles. Both monocytes and macrophages from buffy coat CD14 cells were tested for phagocytic uptake using pHRodo beads, which fluoresce only when taken into acidic endosomes. Briefly, monocytes or macrophages were cultured with 1-2 uL of pHRodo *Escherichia coli* bioparticles (Life Technologies, Thermo Fisher) for 1 h, then the medium was taken off and cells washed to remove non-phagocytosed particles. Phagocytosis was assessed using an EVOS microscope (Thermo Fisher), images captured and cellular uptake of beads quantified using ImageJ software (NIH freeware, https:imagej.nih.gov/ij). Using pHRodo beads in these studies gives an accurate assessment because the beads are clear until phagocytosed and fluoresce once exposed to the acidic environment of the phagolysosome. Phagocytosis was quantified from EVOS images (FIG. 3A), assessing total cell numbers per field, total cells containing fluorescent beads, and then number of beads per cell. Quantification of phagocytosis using this method demonstrated that there was no difference in uptake between monocytes and macrophages (FIG. 3B). Further analysis indicated that stimulation of macrophages with TNF-α and poly I:C had no significant effect on phagocytosis (data not shown).

Polarization of Macrophages at Harvest

The phenotype analysis indicated that the macrophages at harvest are not polarized, but they do demonstrate high CD206 and CD169 expression characteristic of alternatively activated macrophages (FIG. 6). IFN-γ and IL-4 stimulation was used to determine whether the macrophages at harvest were capable of responding to polarizing cytokine exposure. The capacity to polarize toward defined differentiated macrophages was examined by treating day 7 macrophages with interferon (IFN)-γ (50 ng/mL) or interleukin (IL)-4 (20 ng/mL) for 48 h to induce polarization to M1 or M2 phenotype (or M[IFNγ] versus M[IL-4], respectively). After 48 h, the cells were visualized by EVOS bright-field microscopy, then harvested and phenotyped as before. At day 2 of polarization, there was a morphological difference in the cultures, with IFN-γ-treated macrophages showing rounded, angular shape (FIG. 4A), whereas IL-4-treated macrophages showed characteristic spindle shaped morphology. Although there was no significant difference in the 25F9 marker expression between the cultures, the IL-4-treated cells were able to significantly up-regulate CD206, characteristic of polarized M2a macrophages (FIG. 4B). This polarization is characteristic of macrophages in vitro and does not necessarily predict functional capacity in recipients.

Cytokine and Growth Factor Secretion Profile of Macrophages

A final aspect of cell product assessment was determination of macrophage factor secretion profile at rest and after stimulation (FIG. 5). Macrophages were generated from healthy donor buffy coats as before, and either left untreated or stimulated with tumor necrosis factor (TNF)-α (50 ng/mL, Peprotech) and polyinosinic:polycytidylic acid (poly I:C, a viral homolog which binds TLR3, 1_g/mL, Sigma) to mimic the conditions present in the inflamed liver, or lipopolysaccharide (LPS, 100 ng/mL, Sigma) plus IFN-γ (50

IU/mL, Peprotech) to produce a maximal macrophage activation. Day 7 macrophages were incubated overnight and supernatants collected and spun down to remove debris, then stored at −80° C. until testing. Secretome analysis was performed using a 27-plex human cytokine kit and a 9-plex matrix metalloprotease kit run on aMagpix multiplex enzyme linked immunoassay plate reader (BioRad). Macrophages expressed low levels of IL-1Ra, IL-10 and vascular endothelial growth factor (VEGF) at rest. Stimulation with TNF-α and poly I:C was used to mimic an inflamed environment and led to significant increases in production of the pro-regenerative/anti-inflammatory factors VEGF, IL-10 and IL-1Ra, but no increase in IL-12. IL-10 expression was not increased strongly by LPS/IFN-γ stimulation, but conversely IL-12 expression was strongly increased by LPS/IFN-γ. TNF-α/poly I:C stimulation increased expression of CCL3, 4 and 5 but with no significant increase in CCL2. Macrophages constitutively expressed high levels of MMP 7, 9 and 12 with low expression of MMP3. This MMP expression was not modulated significantly after stimulation or polarization, and there was negligible expression of MMPs 1, 7, 8, 10 and 11 (data not shown).

Example 3. Process Validation Cirrhotic Patients

Culturing Monocytes from Patient Samples

Monocytes cultured from leukapheresis from Prodigy isolation were cultured at 2×10$^6$ monocytes per cm$^2$ and per mL in culture bags (MACS GMP differentiation bags, Miltenyi) with GMP-grade TexMACS (Miltenyi) and 100 ng/mL M-CSF. Monocytes were cultured with 100 ng/mL GMP-compliant recombinant human M-CSF (R&D Systems). Cells were cultured in a humidified atmosphere at 37° C., with 5% CO2 for 7 days. A 50% volume media replenishment was carried out twice during culture (days 2 and 4) with 50% of the culture medium removed, then fed with fresh medium supplemented with 200 ng/mL M-CSF (to restore a final concentration of 100 ng/mL).

Process Validation

The cell culture and identity data was used to design the GMP process which was then validated. A set of markers were chosen from the broad phenotyping panel to use as product Release Criteria inclusive of cell identity and functional markers. These were expression of CD45 and CD14 for lineage determination and 25F9 as a marker of macrophage maturity. In addition CD206 was chosen as a surrogate marker for phagocytosis and scavenging capacity, which would effectively identify the development of suitable functional macrophages. The viability stain DRAQ7 was included as a final component of the GMP Release Criteria panel. For further information on the cell product, a second phenotyping set was used, termed the Extended Panel, which assesses expression of CD163, CD169 and CCR2. This panel was validated on leukapheresis donations from 7 cirrhotic volunteers.

Monocyte and macrophage cell surface marker expression was analyzed using either a FACSCanto II (BD Biosciences) or MACSQuant 10 (Miltenyi) flow cytometer. Approximately 20000 events were acquired for each sample. Cell surface expression of leukocyte markers in freshly isolated and day 7 matured cells was carried out by incubating cells with specific antibodies (final dilution 1:100). Cells were incubated for 5 min with FcR block (Miltenyi) then incubated at 4° C. for 20 min with antibody cocktails. Cells were washed in PEA, and dead cell exclusion dye DRAQ7 (BioLegend) was added at 1:100. Cells were stained for a range of surface markers as follows: CD45-VioBlue, CD14-PE or CD14-PerCPVio700, CD163-FITC, CD169-PE and CD16-APC (all Miltenyi), CCR2-BV421, CD206-FITC, CXCR4-PE and CD115-APC (all BioLegend), and 25F9-APC and CD115-APC (eBioscience). Both monocytes and macrophages were gated to exclude debris, doublets and dead cells using forward and side scatter and DRAQ7 dead cell discriminator (BioLegend) and analysed using FlowJo software (Tree Star). From the initial detailed phenotyping, a panel was developed as Release Criteria (CD45-VB/CD206-FITC/CD14-PE/25F9-APC/DRAQ7) that defined the development of a functional macrophage from monocytes. Macrophages were determined as having mean fluorescence intensity (MFI) five times higher than the level on day 0 monocytes for both 25F9 and CD206. A second panel was developed which assessed other markers as part of an Extended Panel, composed of CCR2-BV421/CD163-FITC/CD169-PE/CD14-PerCP-Vio700/CD16-APC/DRAQ7), but was not used as part of the Release Criteria for the cell product.

CD14+ cells were selected using the CliniMACS Prodigy device, and the cells were cultured as described above. The levels of expression of each marker are shown on day 0 enriched monocytes and corresponding day 7 macrophages in FIG. 6. Differentiated cells retain CD45+ CD14+ expression and 25F9, CD206, CD169 and CD163 was significantly elevated in macrophages. CCR2 becomes significantly down-regulated in macrophages when compared with monocytes. The migratory capacity of the macrophages post-harvest was also assessed using transwell chemotaxis assay and confirmed that they retained the ability to migrate to suitable targets in vitro despite the down-regulation of CCR2 (data not shown).

Stability of the Monocytes Post-Harvest from Cirrhotic Patients

Stability studies were performed on macrophages stored at controlled room temperature (21-22° C.) in optimum excipient, as determined during process optimization (clinical grade 0.9% saline with 0.5% HAS). Various excipients were tested during process development including PBS/EDTA buffer; PBS/EDTA buffer with 0.5% HAS (Alburex), 0.9% saline alone or saline with 0.5% HAS. The 0.9% saline (Baxter) with 0.5% HAS excipient was found to maintain optimal cell viability and phenotype (data not shown). The stability of the macrophages from cirrhotic donors after harvest was investigated in three process optimization runs, and a more limited range of time points assessed in the process validation runs (n=3). After harvest and re-suspension in excipient (0.9% saline for infusion, 0.5% human serum albumin), the bags were stored at ambient temperature (21-22° C.) and samples taken at 0, 2, 4, 6, 8, 12, 24, 30 and 48 h post-harvest. The release criteria antibody panel was run on each sample, and viability and mean fold change from day 0 was measured from geometric MFI of 25F9 and CD206. After sampling at each time-point the cells were assessed for phenotype and viability. Data from all three Process Optimization runs indicated that both cell viability and phenotype (25F9/CD206 MFI) were maintained to 48 hrs post-harvest (FIG. 7), indicating that the process reproducibly produces a very stable cell product. Release criteria were thus established that the macrophages should be CD45/CD14 positive, with a viability greater than 80%, and have a MFI for 25F9 and CD206>5 fold higher than the MFI of the original monocytes at day 0. All final results for Release Criteria process validation including stability are detailed in Table 1.

TABLE I

Data from process validation runs 1-3.

| Acceptance criteria | Expected result | Actual result Patient 1 | Patient 2 | Patient 3 |
|---|---|---|---|---|
| Selection (D0) CD 14 yield | ≥40% | 41% | 59% | 64% |
| Final macrophage yield (viable cell number) | $1 \times 10^7$ to $1 \times 10^9$ | $5.11 \times 10^8$ | $5.73 \times 10^8$ | $2.9 \times 10^8$ |
| Harvest (D7) Macrophage viability | ≥80% | 87% | 95% | 87% |
| Harvest (D7) 25F9 MFI fold increase | ≥5 | 17 | 19 | 26 |
| Harvest (D7) CD206 MFI fold increase | ≥5 | 33 | 28 | 82 |
| Stability (48 h) Macrophage Viability | ≥80% | 91% | 88% | 86% |
| Stability (48 h) 25F9 MFI fold increase | ≥5 | 18 | 8 | 11 |
| Stability (48 h) CD206 MFI fold increase | ≥5 | 21 | 19 | 41 |

Details include the parameters that will be used as release criteria for final product.

Example 4. Autologous Monocyte-Derived Macrophage Therapy for Human Trial

A. Single Ascending Dose (SAD) Phase I Trial
Patient Recruitment

Eligibility criteria were age range of 18 to 75 years, MELD range of 10.00 to 16 and cirrhosis was defined by any one of the following: alcohol related liver disease (ALD), primary biliary cirrhosis (PBC), non-alcoholic fatty liver disease (NAFLD), cryptogenic cirrhosis, hemochromatosis, alpha-1-antitrypsin deficiency, treated (sustained viral response) hepatitis C. Exclusion criteria were portal hypertensive bleeding in the preceding 3 months, ascites not well controlled with diuretic therapy in the preceding 3 months, encephalopathy requiring hospitalisation for treatment in the previous 3 months, hepatocellular carcinoma (dysplastic or indeterminate nodules to be excluded, regenerative or other nodules to be included), previous diagnosis of hepatocellular carcinoma, previous recipient of organ transplant or previous recipient of tissue. Other exclusion criteria include; alcohol or drug abuse, residence distant from study site, non-compliance or inability to co-operate, clinically relevant acute illness compromising participation in the study, presence or history of cancer within the past 5 years, pregnancy or breastfeeding.

TABLE 2

Characteristics of patients studied in the SAD phase of the MATCH study.

| Patient | Dose (cells) | Aetiology | History | Baseline MELD |
|---|---|---|---|---|
| S03 | $10^7$ | Alcohol | Cirrhosis diagnosis February 2015<br>Abstinent since December 2014<br>Portal hypertension, varices & ascites | 13 |
| S04 | $10^7$ | PBC3 | Cirrhosis diagnosis 2005<br>No history of decompensation | 11 |
| S05 | $10^7$ | Alcohol | Cirrhosis diagnosis May 2015<br>Pre-Dx alcohol 100 units/week, reduced to 1-10/week<br>Portal hypertension & varices | 14 |
| S06 | $10^8$ | Alcohol | Cirrhosis diagnosis January 2013<br>Abstinent since March 2015<br>Portal hypertension; no history of decompensation | 13 |
| S07 | $10^8$ | Alcohol | Cirrhosis diagnosis January 2008<br>Abstinent 3+ years<br>Portal hypertension & variceal bleeding | 10 |
| S08 | $10^8$ | HCV | Cirrhosis diagnosis 2004<br>SVR Nov 2014<br>Variceal bleeding & ascites | 13 |
| S09 | $7.5 \times 10^8$ | NASH | Cirrhosis diagnosis January 2016<br>Abdominal obesity<br>Portal hypertension; no history of decompensation | 10 |

TABLE 2-continued

Characteristics of patients studied in the SAD phase of the MATCH study.

| Patient | Dose (cells) | Aetiology | History | Baseline MELD |
|---|---|---|---|---|
| S10 | 7.5 × 10$^8$ | Alcohol | Cirrhosis diagnosis 2013 Abstinent for 3+ years Portal hypertension & variceal bleeding | 13 |
| S11 | 7.5 × 10$^8$ | Alcohol | Cirrhosis diagnosis 2013 Abstinent since 2014 Portal hypertension, variceal bleeding & ascites | 11 |

Autologous Unpolarized Macrophage Product

CD14+ monocytes are isolated from the leukapheresis product utilising the CliniMACS Prodigy® closed system. CD14+ monocytes are cultured for 7 days in low adhesion culture bags (Miltenyi) in the presence of TexMACS™ serum-free media (Miltenyi) and 100 ng/ml M-CSF (R&D Systems) as described above. A 33% medium change is given at days 3 and 5. In addition, the final product is assessed for markers of macrophage phenotype (25F9 and CD14) and functional markers (CD206). Assessment of viability is performed by DRAQ7 staining as described above. The final product is harvested and prepared for infusion as a population of ≤1×10$^7$; ≤1×10$^8$ or ≤1×10$^9$ cells in 125 mL 0.9% Saline (Baxter) and 0.5% Human Albumin Solution. The product is presented in a transfer bag (Terumo 150 mL Transfer Bag) and over wrapped prior to transfer to the investigator site for use within 48 hours.

Study Design

The first phase of the study is designed as a standard 3+3 design to test cell safety and tolerability in humans. The autologous macrophages are administered to participants in a dose escalation manner with one infusion at three different doses of cells; 10$^7$, 10$^8$, 10$^9$. Each dose of cells is administered to three participants. Following differentiation of the macrophages from the monocytes on day 7 after apheresis, participants return to the clinical research unit. Prior to the administration of the autologous macrophage product, participants are infused with 10 mg IV chlorphenamine, 100 mg IV hydrocortisone and 250 mls normal saline via an intravenous cannula for 30 minutes. The macrophage product is administered over 30 minutes intravenously followed by infusion of 250 mls saline over 15-20 mins. Blood tests are carried out on the participants at 7 and 14 days and then 30, 60, 90, 180, 360 days post infusion.

Regenerative Macrophages from Cirrhotic Patients

It has been demonstrated that regenerative macrophages can be derived from cirrhotic patients. Gene expression of several markers including CCL2, MMP9, IL10, CCL3 were not significantly different in ex vivo differentiated macrophages from healthy and cirrhotic patients (FIG. 8).

For the MATCH trial, MELD was measured at various time points. The first measurement was taken 3-6 months before initial screening. This data point is referred to as d-120 however the actual blood test for each patient was taken at different time points within the 3-6 month period. MELD was also measured at the initial screen i.e. baseline (d-14) and then d7, d14, d30, d60, d90, d180, and d360. d0 is the day the of administration of the macrophage product.

MELD consists of three components; bilirubin (BIL), creatinine (CRE) and international normalized ratio (INR), and these are combined in the following formula to generate a MELD score.

MELD=10*[(0.957*In(CRE (mmol/l)*0.011312217))+(0.378*In(BIL (mmol/l)*0.058479532))+(1.12*In(INR))]+6.43 (Huo et al. Journal of hepatology 2005; 42(6):826-32).

None of the components of MELD can have a negative contribution and MELD scores are rounded to the nearest whole integer. Table 3 shows the MELD data for all subjects in the MATCH trial. The Δ MELD for all patients was calculated relative to baseline (d-14) where a negative value shows an improvement in clinical status. FIG. 9 shows the average Δ MELD for all patients. The most significant response is from S05 in whom a transient reduction of 6 points of MELD was observed. The macrophage therapy is thought to have a greater effect on cirrhotic patients whose underlying aetiology is hepatocyte driven. As the aetiology of patient S04 was primary biliary cholangitis (PBC) which is not thought to be hepatocyte driven, it was not surprising that less of a response to treatment was observed in this patient. respond.

To understand the mechanistic contribution of unpolarized macrophage therapy to the ΔMELD, the contribution of each of the component of MELD to the ΔMELD was assessed and illustrated as show in FIG. 10. The results suggest that MELD score reduces for two of the three components; BIL and INR with a 62% of the variation in ΔMELD explained by the contribution of BIL, and the remainder from INR. No significant changes were observed in the MELD score for the contribution of the CRE component. These results suggest that the observed improvements in MELD are due to direct improvements in liver function. Bilirubin is a by-product of haemoglobin metabolism as a result of red blood cells dying. Circulating bilirubin is glucuronidated by hepatocytes and then excreted via the bile duct. Thus BIL is a measure of hepatocyte health and function. INR is a consequence of the liver's capacity to synthesize vitamin K-derived clotting factors, and while a less direct measure of hepatocyte function than BIL, also suggests an improvement in liver health. By contrast, CRE is a kidney marker, and is a surrogate for multi-organ failure associated with liver cirrhosis. Thus, the data shows that not only does unpolarized therapy have a beneficial effect on MELD, but that the effect is driven by an improvement in liver function, consistent with the proposed mechanism of action of the treatment.

TABLE 3

MELD data from the MATCH trial

| | | Days post dosing | | | | | | | | |
|---|---|---|---|---|---|---|---|---|---|---|
| | | −120* | −14 | 7 | 14 | 30 | 60 | 90 | 180 | 360 |
| S03 | INR | 1.3 | 1.4 | 1.3 | 1.4 | 1.3 | 1.3 | 1.3 | 1.3 | 1.3 |
| | CRE | 83 | 78 | 75 | 77 | 73 | 78 | 76 | 71 | 74 |
| | BIL | 26 | 32 | 24 | 30 | 33 | 28 | 27 | 24 | 29 |
| | MELD | 11 | 13 | 11 | 12 | 12 | 11 | 11 | 11 | 11 |
| | Δ MELD | −2 | 0 | −2 | −1 | −1 | −2 | −2 | −2 | −2 |
| S04 | INR | 0.8 | 0.8 | 0.9 | 0.9 | 0.9 | 0.8 | 0.8 | 0.9 | 0.9 |
| | CRE | 69 | 68 | 75 | 63 | 62 | 73 | 73 | 72 | 69 |
| | BIL | 65 | 54 | 58 | 64 | 63 | 55 | 52 | 55 | 49 |
| | MELD | 11 | 11 | 11 | 11 | 11 | 11 | 11 | 11 | 10 |
| | Δ MELD | 0 | 0 | 0 | 0 | 0 | 0 | 0 | 0 | −1 |
| S05 | INR | 1.2 | 1.4 | 1.3 | 1.3 | 1.2 | 1.2 | 1.2 | 1.3 | 1.3 |
| | CRE | 84 | 77 | 90 | 85 | 82 | 77 | 76 | 86 | 88 |
| | BIL | 30 | 44 | 26 | 26 | 29 | 16 | 19 | 25 | 31 |
| | MELD | 11 | 14 | 11 | 11 | 10 | 8 | 9 | 11 | 12 |
| | Δ MELD | −3 | 0 | −3 | −3 | −4 | −6 | −5 | −3 | −2 |
| S06 | INR | 1.7 | 1.6 | 1.5 | 1.7 | 1.6 | 1.6 | 1.6 | 1.6 | 1.5 |
| | CRE | 62 | 57 | 63 | 58 | 63 | 66 | 57 | 63 | 60 |
| | BIL | 38 | 22 | 25 | 29 | 27 | 24 | 35 | 35 | 18 |
| | MELD | 15 | 13 | 12 | 14 | 13 | 13 | 14 | 14 | 11 |
| | Δ MELD | 2 | 0 | −1 | 1 | 0 | 0 | 1 | 1 | −2 |
| S07 | INR | 1.3 | 1.2 | 1.2 | 1.2 | 1.2 | 1.2 | 1.2 | 1.2 | 1.2 |
| | CRE | 64 | 67 | 64 | 59 | 58 | 62 | 60 | 57 | 59 |
| | BIL | 34 | 27 | 15 | 22 | 31 | 20 | 16 | 20 | 27 |
| | MELD | 12 | 10 | 8 | 9 | 11 | 9 | 8 | 9 | 10 |
| | Δ MELD | 2 | 0 | −2 | −1 | 1 | −1 | −2 | −1 | 0 |
| S08 | INR | 1.3 | 1.3 | 1.3 | 1.2 | 1.3 | 1.3 | 1.3 | 1.3 | 1.3 |
| | CRE | 72 | 72 | 76 | 80 | 79 | 72 | 70 | 71 | 69 |
| | BIL | 37 | 43 | 37 | 31 | 40 | 28 | 29 | 56 | 67 |
| | MELD | 12 | 13 | 12 | 11 | 13 | 11 | 11 | 14 | 15 |
| | Δ MELD | −1 | 0 | −1 | −2 | 0 | −2 | −2 | 1 | 2 |
| S09 | INR | 1.2 | 1.2 | 1.1 | 1.1 | 1.1 | 1.1 | 1.1 | 1.2 | 1.1 |
| | CRE | 58 | 68 | 60 | 60 | 59 | 66 | 60 | 67 | 68 |
| | BIL | 25 | 25 | 15 | 16 | 22 | 10 | 20 | 14 | 17 |
| | MELD | 10 | 10 | 7 | 7 | 8 | 7 | 8 | 8 | 7 |
| | Δ MELD | 0 | 0 | −3 | −3 | −2 | −3 | −2 | −2 | −3 |
| S10 | INR | 1.3 | 1.4 | 1.4 | 1.4 | 1.4 | 1.4 | 1.3 | 1.3 | 1.2 |
| | CRE | 66 | 60 | 65 | 62 | 62 | 74 | 52 | 67 | 67 |
| | BIL | 43 | 37 | 35 | 38 | 40 | 45 | 36 | 44 | 41 |
| | MELD | 13 | 13 | 13 | 13 | 13 | 14 | 12 | 13 | 12 |
| | Δ MELD | 0 | 0 | 0 | 0 | 0 | 1 | −1 | 0 | −1 |
| S11 | INR | 1.2 | 1.2 | 1.2 | 1.3 | 1.3 | 1.3 | 1.3 | 1.3 | 1.2 |
| | CRE | 64 | 67 | 63 | 61 | 63 | 59 | 65 | 63 | 63 |
| | BIL | 23 | 34 | 27 | 27 | 27 | 30 | 30 | 30 | 47 |
| | MELD | 10 | 11 | 10 | 11 | 11 | 11 | 11 | 11 | 10 |
| | Δ MELD | −1 | 0 | −1 | 0 | 0 | 0 | 0 | 0 | −1 |

*d −120 is not an absolute time point, these data points were collected in 3-6 month time frame before the start of the trial (screening).

Also for the MATCH trial the enhanced liver fibrosis (ELF), which provides a non-invasive measurement of fibrosis, was measured at various time points including at screening (d-14), d30, d60, d90, d180, and d360. d0 being the day the of administration of the macrophage product. FIG. 11 shows the ELF score for all patients in the MATCH study, whilst FIG. 12 shows the ΔELF for all patients in the MATCH study FIGS. 13, 14, and 5 provide the breakdown of each of the components of the ELF score—HA values, PNIIIP and TIMP1, respectively. The graphs show a general reduction in enhanced liver fibrosis over the 360 day period measured.

Precisely cleaved N-terminal propeptide of type III collagen (PRO-C3) and peptide of helical collagen type III degradation (C3M) were measured at various time points including at screening, screening (d-14), d30 and d90.

TABLE 4

PRO-C3 data from the MATCH trial

| | Screening | Day 30 | Day 90 |
|---|---|---|---|
| S03 | 14.8 | 19.4 | 13.9 |
| S04 | 77.0 | 90.5 | 71.8 |
| S05 | 112.3 | 84.4 | 74.3 |
| S06 | 33.0 | 29.2 | 25.6 |
| S07 | 18.3 | 21.4 | 20.3 |
| S08 | 19.0 | ND | 15.8 |
| S09 | 24.0 | 18.1 | 16.6 |
| S10 | 37.2 | 37.4 | 35.7 |
| S11 | 57.4 | 46.1 | 43.7 |

The data for PRO-C3 demonstrates a reduction in fibrosis formation.

TABLE 5

| | C3M data from the MATCH trial | | |
|---|---|---|---|
| | Screening | Day 30 | Day 90 |
| S03 | 26.4 | 20.1 | 18.9 |
| S04 | 23.2 | 23.6 | 16.8 |
| S05 | 21.0 | 17.1 | 15.1 |
| S06 | 11.9 | 10.9 | 10.8 |
| S07 | 12.3 | 11.5 | 9.7 |
| S08 | 12.0 | ND | 12.5 |
| S09 | 13.5 | 10.0 | 12.5 |
| S10 | 11.8 | 11.5 | 11.2 |
| S11 | 13.1 | 11.2 | 13.6 |

B. Phase II Trial

A randomised controlled study is undertaken. 28 participants are randomised to receive standard medical care. 28 participants receive a total of 3 infusions of $10^9$ macrophages 30 days apart.

Autologous Unpolarized Macrophage Product

Monocytes cultured from leukapheresis from Prodigy isolation were cultured at $2 \times 10^6$ monocytes per $cm^2$ and per mL in culture bags (MACS GMP differentiation bags, Miltenyi) with GMP-grade TexMACS (Miltenyi) and 100 ng/mL M-CSF. Monocytes were cultured with 100 ng/mL GMP-compliant recombinant human M-CSF (R&D Systems). Cells were cultured in a humidified atmosphere at 37° C., with 5% CO2 for 7 days. A 50% volume media replenishment was carried out once during culture (on day 4) with 50% of the culture medium removed, then fed with fresh medium supplemented with 200 ng/mL M-CSF (to restore a final concentration of 100 ng/mL). Advantageously, this single feed (compared to two feeds) reduces cell manipulations and cell handling steps, leading to a reduction in costs as well as a reduction in cell losses.

CD14+ monocytes are isolated from the leukapheresis product and characterised before transfer to the investigator site, as described above.

Measured Outcomes:

Patients who receive infusions are assessed for outcome by one or more of the following assessments/measurements: MELD and delta MELD; UKELD and delta UKELD; Transient Elastography (Fibroscan™, Echosens, France) (Fraquelli et al. Gut, 2007; 56(7): 968-73)—a non-invasive method for assessing liver fibrosis at screening, Day 90, Day 180 and Day 360; Enhanced Liver Fibrosis (ELF) Test-ELISA assays for matrix components and enzymes involved in their turnover (Hyaluronic Acid, Tissue Inhibitor of Matrix Metalloproteinase 1 (TIMP-1), Procollagen Type III (PIIINP) calculated ELF score-relates to the level of liver fibrosis; 31-P-MRS and liver MRI scan: at randomisation and at day 90 post therapy non-invasive and quantitative measure of liver metabolism and regenerative activity; MRI for Liver volume and blood flow. Other ways of assessing outcome includes CLDQ (Chronic Liver Disease Questionnaire) (Younossi et al. Gut 1999; 45(2); 295-300) and those described by Newsome et al. Gastroenterol Hepatol. 2018; 3: 25-36).

Additional analysis may include measuring for changes in protein markers: During extracellular matrix (ECM) turnover, proteolytically cleaved matrix degradation fragments, or neoepitopes, are released into the systemic circulation. Cleavage of each ECM protein by specific MMPs generates a unique neoepitope. These neoepitopes are possibly more accurate diagnostic and prognostic markers for individual fibroproliferative diseases than their protein of origin. Methods for detecting such specific protein fragments and identifying and quantifying disease include Protein Fingerprint™ technology (Nordic Bioscience). These novel serum biomarkers have been shown to identify patients with progressive fibrosis and permit monitoring of the response to antifibrotic therapy, and also correlate with portal hypertension in patients with cirrhosis.

REFERENCES

Campbell J D, Piechaczek C, Winkels G, Schwamborn E, Micheli D, Hennemann S, Schmitz J. Isolation and generation of clinical-grade dendritic cells using the CliniMACS system. Methods Mol Med. 2005; 109:55-70. PubMed PMID: 15585913.

Fraquelli M, Rigamonti C, Casazza G, Conte D, Donato M F, Ronchi G, et al. Reproducibility of transient elastography in the evaluation of liver fibrosis in patients with chronic liver disease. Gut. 2007; 56(7): 968-73

Fraser A R, Pass C, Burgoyne P, Atkinson A, Bailey L, Laurie A, W A McGowan N, Hamid A, Moore J K, Dwyer B J, Turner M L, Forbes S J, Campbell J D M. Development, functional characterization and validation of methodology for GMP-compliant manufacture of phagocytic macrophages: A novel cellular therapeutic for liver cirrhosis. Cytotherapy. 2017 September; 19(9):1113-1124. doi: 10.1016/j.jcyt.2017.05.009. Epub 2017 Jun. 30. PubMed PMID: 28673774; PubMed Central PMCID: PMC5571439

Hale C, Yeung A, Goulding D, Pickard D, Alasoo K, Powrie F, Dougan G, Mukhopadhyay S. Induced pluripotent stem cell derived macrophages as a cellular system to study salmonella and other pathogens. PLoS One. 2015 May 6; 10(5):e0124307. doi: 10.1371/journal.pone.0124307. eCollection 2015. PubMed PMID: 25946027; PubMed Central PMCID: PMC4422593.

Huo T I, Wu J C, Lin H C, Lee F Y, Hou M C, Lee P C, Chang F Y, Lee S D. Evaluation of the increase in model for end-stage liver disease (DeltaMELD) score over time as a prognostic predictor in patients with advanced cirrhosis: risk factor analysis and comparison with initial MELD and Child-Turcotte-Pugh score. J Hepatol. 2005 June; 42(6):826-32. Epub 2005 Mar. 31. PubMed PMID: 15885353.

Irvine K, Wockner L F, Shanker M, Fagan K J, Horsfall L U, Fletcher L M, Ungerer J P J, Pretorius C J, Miller G C, Clouston A D, Lampe G and Powell E E. The Enhanced liver fibrosis score is associated with clinical outcomes and disease progression in patients with chronic liver disease. Liver International 2016, 370-377 ISSN 1478-3223

Martinez F O, Gordon S. The M1 and M2 paradigm of macrophage activation: time for reassessment. F1000Prime Rep. 2014 Mar. 3; 6:13. doi: 10.12703/P6-13.eCollection 2014. Review. PubMed PMID: 24669294; PubMed Central PMCID:PMC3944738.

Moore J K, Mackinnon A C, Wojtacha D, Pope C, Fraser A R, Burgoyne P, Bailey L, Pass C, Atkinson A, Mcgowan N W, Manson L, Turner M L, Campbell J D, Forbes S J. Phenotypic and functional characterization of macrophages with therapeutic potential generated from human cirrhotic monocytes in a cohort study. Cytotherapy. 2015 November; 17(11):1604-16. doi: 10.1016/j.jcyt.2015.07.016. Epub 2015 Sep. 3. PubMed PMID: 26342993; PubMed Central PMCID: PMC4596388.

Mucci A, Kunkiel J, Suzuki T, Brennig S, Glage S, Kühnel M P, Ackermann M, Happle C, Kuhn A, Schambach A, Trapnell B C, Hansen G, Moritz T, Lachmann N. Murine iPSC-Derived Macrophages as a Tool for Disease Modeling of Hereditary Pulmonary Alveolar Proteinosis due to Csf2rb Deficiency. Stem Cell Reports. 2016 Aug. 9; 7(2):292-305. doi: 10.1016/j.stemcr.2016.06.011. Epub 2016 Jul. 21. PubMed PMID: 27453007; PubMed Central PMCID: PMC4982988.

Murray P J, Allen J E, Biswas S K, Fisher E A, Gilroy D W, Goerdt S, Gordon S, Hamilton J A, Ivashkiv L B, Lawrence T, Locati M, Mantovani A, Martinez F O, Mege J L, Mosser D M, Natoli G, Saeij J P, Schultze J L, Shirey K A, Sica A, Suttles J, Udalova I, van Ginderachter J A, Vogel S N, Wynn T A. Macrophage activation and polarization: nomenclature and experimental guidelines. Immunity. 2014 Jul. 17; 41(1):14-20. doi: 10.1016/j.immuni.2014.06.008. PubMed PMID: 25035950; PubMed Central PMCID: PMC4123412.

Nielsen M J, Nedergaard A F, Sun S, Veidal S S, Larsen L, Zheng Q, Suetta C, Henriksen K, Christiansen C, Karsdal M A, Leeming D J. The neo-epitope specific PRO-C3 ELISA measures true formation of type III collagen associated with liver and muscle parameters. Am J Transl Res 2013; 5(3):303-315. ISSN:1943-8141

P N Newsome, R Fox, A L King; Granulocyte colony-stimulating factor and autologous CD133-positive stem-cell therapy in liver cirrhosis (REALISTIC): an open-label, randomised, controlled phase 2 trial. Lancet Gastroenterol Hepatol. 2018; 3: 25-36, Senju S, Koba C, Haruta M, Matsunaga Y, Matsumura K, Haga E, Sasaki Y, Ikeda T, Takamatsu K, Nishimura Y. Application of iPS cell-derived macrophages to cancer therapy. Oncoimmunology. 2014 Jan. 1; 3(1):e27927. Epub 2014 Feb. 14. PubMed PMID: 24800175; PubMed Central PMCID: PMC4008454.

Tacke F. Targeting hepatic macrophages to treat liver diseases. J Hepatol. 2017 June; 66(6):1300-1312. doi: 10.1016/j.jhep.2017.02.026. Epub 2017 Mar. 4. Review. PubMed PMID: 28267621.

Thiele M, Stæhr Madsen B, Fuglsang Hansen J, Detlefsen S, Antonsen S and Krag A. Accuracy of the Enhanced Liver Fibrosis Test vs FibroTest, Elastography, and Indirect Markers in Detection of Advanced Fibrosis in Patients With Alcoholic Liver Disease. Gastroenterology 2018; 154:1369-1379.

van Wilgenburg B, Browne C, Vowles J, Cowley S A. Efficient, long term production of monocyte derived macrophages from human pluripotent stem cells under partly-defined and fully-defined conditions. PLoS One. 2013 Aug. 12; 8(8):e71098. doi: 10.1371/journal.pone.0071098. eCollection 2013. PubMed PMID: 23951090; PubMed Central PMCID: PMC3741356.

Wang P, Koyama Y, Liu X, Xu J, Ma H Y, Liang S, Kim I H, Brenner D A, Kisseleva T. Promising Therapy Candidates for Liver Fibrosis. Front Physiol. 2016 Feb. 16; 7:47. doi: 10.3389/fphys.2016.00047. eCollection 2016. Review. PubMed PMID: 26909046; PubMed Central PMCID: PMC4754444.

Yang C T, Ma R, Axton R A, Jackson M, Taylor A H, Fidanza A, Marenah L, Frayne J, Mountford J C, Forrester L M. Activation of KLF1 Enhances the Differentiation and Maturation of Red Blood Cells from Human Pluripotent Stem Cells. Stem Cells. 2017 April; 35(4):886-897. doi: 10.1002/stem.2562. Epub 2017 Jan. 19. PubMed PMID:28026072; PubMed Central PMCID: PMC5396323.

Yeung A T, Hale C, Xia J, Tate P H, Goulding D, Keane J A, Mukhopadhyay S, Forrester L, Billker O, Skarnes W C, Hancock R E, Dougan G. Conditional-ready mouse embryonic stem cell derived macrophages enable the study of essential genes in macrophage function. Sci Rep. 2015 Mar. 10; 5:8908. doi: 10.1038/srep08908. PubMed PMID: 25752829; PubMed Central PMCID: PMC4354151.

Younossi Z M, Guyatt G, Kiwi M, Boparai N, King D. Development of a disease specific questionnaire to measure health related quality of life in patients with chronic liver disease. Gut. 1999; 45(2):295-300.

Zimmermann H W, Seidler S, Nattermann J, Gassier N, Hellerbrand C, Zernecke A, Tischendorf J J, Luedde T, Weiskirchen R, Trautwein C, Tacke F. Functional contribution of elevated circulating and hepatic non-classical CD14CD16 monocytes to inflammation and human liver fibrosis. PLoS One. 2010 Jun. 10; 5(6):e11049. doi: 10.1371/journal.pone.0011049. PubMed PMID: 20548789; PubMed Central PMCID: PMC2883575.

Zhang H, Xue C, Shah R, Bermingham K, Hinkle C C, Li W, Rodrigues A, Tabita-Martinez J, Millar J S, Cuchel M, Pashos E E, Liu Y, Yan R, Yang W, Gosai S J, VanDorn D, Chou S T, Gregory B D, Morrisey E E, Li M, Rader D J, Reilly M P. Functional analysis and transcriptomic profiling of iPSC-derived macrophages and their application in modeling Mendelian disease. Circ Res. 2015 Jun. 19; 117(1):17-28. doi: 10.1161/CIRCRESAHA.117.305860. Epub 2015 Apr. 22. PubMed PMID: 25904599; PubMed Central PMCID: PMC4565503.

Zhuang L, Pound J D, Willems J J, Taylor A H, Forrester L M, Gregory C D. Pure populations of murine macrophages from cultured embryonic stem cells. Application to studies of chemotaxis and apoptotic cell clearance. J Immunol Methods. 2012 Nov. 30; 385(1-2):1-14. doi: 10.1016/j.jim.2012.06.008. Epub 2012 Jun. 18. PubMed PMID: 22721870.

The invention claimed is:

1. A method of treating liver disease in a human in need thereof, wherein the method comprises administering autologous isolated unpolarized human macrophages in an amount effective for reducing fibrosis, wherein the human in need thereof is a diseased patient with End Stage Liver Disease and having a MELD score of 10 to 16.

2. The method of claim 1, wherein said autologous isolated unpolarized human macrophages are monocyte-derived.

3. The method of claim 1, wherein said autologous isolated unpolarized human macrophages are mature macrophages.

4. The method of claim 1, wherein said autologous isolated unpolarized human are characterised by elevated expression of at least one surface 25F9 or CD206, which is at least five-fold compared to expression in macrophage source cells.

5. The method of claim 4, wherein said autologous isolated unpolarized human macrophages are further characterised by elevated expression of one or more of CD163 and CD169.

6. The method of claim 5, wherein said autologous isolated unpolarized human macrophages are prepared from CD14+ monocytes isolated from peripheral blood of a diseased patient.

7. The method of claim 6, wherein said autologous isolated unpolarized human macrophages are prepared from CD 14+ monocytes which are incubated with M-CSF for 7 days at a concentration of 100 ng/ml.

8. A method of treating fibrosis in a human in need thereof, wherein the method comprises administering one or more doses of unpolarized macrophages in an amount effective for reducing fibrosis, wherein the human in need thereof is a diseased patient with End Stage Liver Disease and having a MELD score of 10 to 16.

9. The method of claim 8 wherein said macrophages are derived from said human's own PBMCs, from healthy donor PBMCs or from stem cells including bone marrow, embryonic stem cells or induced pluripotent stem cells.

10. The method of claim 8, wherein said one or more doses of said macrophages are administered at an interval of approximately 30 days.

11. The method of claim 8, wherein the human in need thereof has cirrhosis, preferably cirrhotic liver disease.

12. A method of treating fibrosis in a human in need thereof with unpolarized macrophages, the method comprising administering 3 doses of the macrophages to said human wherein the first dose is on day 1, the second dose is on day 30 and the third dose is on day 60, wherein the treatment is in an amount effective for reducing fibrosis, wherein the human in need thereof is a diseased patient with cirrhotic liver disease having a MELD score of 10 to 16, and wherein the patient has End Stage Liver Disease.

13. The method of claim 1, wherein said autologous isolated unpolarised human macrophages are administered intravenously.

14. The method of claim 8, wherein said macrophages are administered intravenously.

15. The method of claim 1, wherein the method comprises administering one or more doses comprising from $1\times10^7$ to $1\times10^9$ of said autologous isolated unpolarised human macrophages.

16. The method of claim 8, wherein the method comprises administering one or more doses comprising from $1\times10^7$ to $1\times10^9$ of said macrophages.

17. The method of claim 1, wherein said liver disease is liver cirrhosis.

* * * * *